United States Patent
Bradner et al.

(10) Patent No.: US 9,458,165 B2
(45) Date of Patent: Oct. 4, 2016

(54) DOT1L INHIBITORS

(71) Applicant: Dana-Farber Cancer Institute, Inc., Boston, MA (US)

(72) Inventors: James E. Bradner, Weston, MA (US); Jun Qi, Sharon, MA (US); Alexander Federation, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/838,142

(22) Filed: Aug. 27, 2015

(65) Prior Publication Data

US 2016/0060269 A1    Mar. 3, 2016

Related U.S. Application Data

(60) Provisional application No. 62/042,594, filed on Aug. 27, 2014.

(51) Int. Cl.
*A61K 31/519* (2006.01)
*C07D 487/04* (2006.01)

(52) U.S. Cl.
CPC .................................. *C07D 487/04* (2013.01)

(58) Field of Classification Search
CPC .................................................... C07D 487/04
See application file for complete search history.

(56) References Cited

U.S. PATENT DOCUMENTS

| 2012/0142625 A1 | 6/2012 | Olhava et al. |
| 2014/0051654 A1 | 2/2014 | Olhava et al. |
| 2014/0100184 A1 | 4/2014 | Song et al. |

FOREIGN PATENT DOCUMENTS

| WO | WO 2012/082436 | 6/2012 |
| WO | WO 2013/055397 | 4/2013 |
| WO | WO 2015/017311 | 2/2015 |

OTHER PUBLICATIONS

McLean et al. The emerging roles of DOT1L in leukemia and normal development. Leukemia (2014) 28, 2131-2138.*
PCT Notification of Transmittal of the International Search Report and the Written Opinion for International Application No. PCT/US2014/048375 dated Dec. 23, 2014, 15 pages.

* cited by examiner

*Primary Examiner* — Brian McDowell
(74) *Attorney, Agent, or Firm* — Fish & Richardson P.C.

(57) ABSTRACT

Provided herein are inhibitors of DOT1L of formula (I) useful for treating diseases or disorders associated with DOT1L:

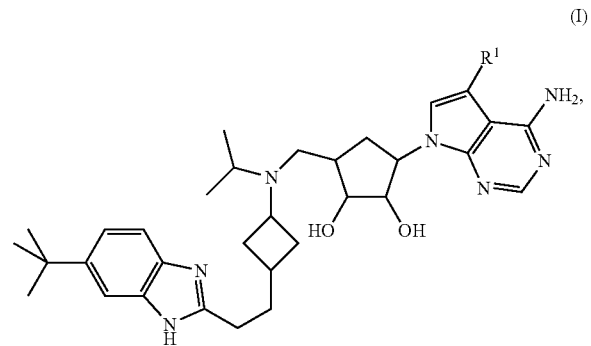

(I)

in which $R^1$ is defined in the specification. An exemplary DOT1L inhibitor provided herein exhibits a biological half-life of 12.6 h. Methods for treating diseases associated with DOT1L are also provided.

15 Claims, 8 Drawing Sheets

DOT1L INHIBITORS

CROSS-REFERENCE TO RELATED APPLICATIONS

This application claims the benefit of U.S. Provisional Application Ser. No. 62/042,594, filed Aug. 27, 2014, the disclosure of which is incorporated herein by reference in its entirety.

TECHNICAL FIELD

This invention relates to compounds that bind to histone H3-lysine79 (H3K79) methyl transferase (DOT1L), and more particularly to compounds which are inhibitors DOT1L, and compositions and method of treatment related thereto.

BACKGROUND

Histone H3-lysine79 (H3K79) methyl transferase (DOT1L) has been shown to play roles in normal cell differentiation as well as initiation of acute leukemia. DOT1L specifically catalyzes methylation of the histone H3-lysine79 (H3K79) residue located in the nucleosome core structure. DOT1L appears to be necessary and sufficient for the initiation and maintenance of leukemia with MLL (mixed lineage leukemia) gene translocations. DOT1L catalyzes an SN2 reaction of the H3K79 ε-NH2 of the substrate nucleosome with the methyl group of S-(5'-adenosyl)-L-methionine (SAM), the enzyme co-factor.

SUMMARY

The present application provides, inter alia, a compound of Formula (I):

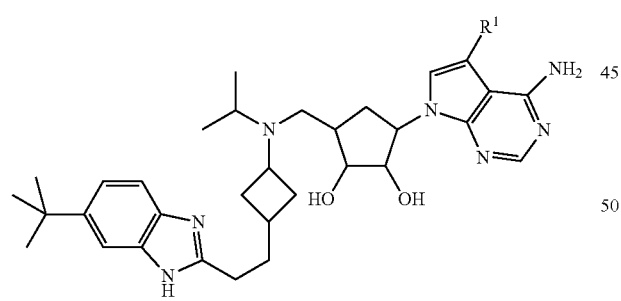

(I)

or a pharmaceutically acceptable salt thereof, wherein $R^1$ is selected from the group consisting of CN, halo, and $C_{1-4}$ haloalkyl.

In some embodiments, $R^1$ is halo. In some embodiments, $R^1$ is chloro or bromo. In some embodiments, $R^1$ is chloro. In some embodiments, $R^1$ is bromo.

In some embodiments, $R^1$ is $C_{1-4}$ haloalkyl. In some embodiments, $R^1$ is trifluoromethyl.

In some embodiments, $R^1$ is CN.

In some embodiments, the compound of Formula (I) is a compound of Formula (Ia):

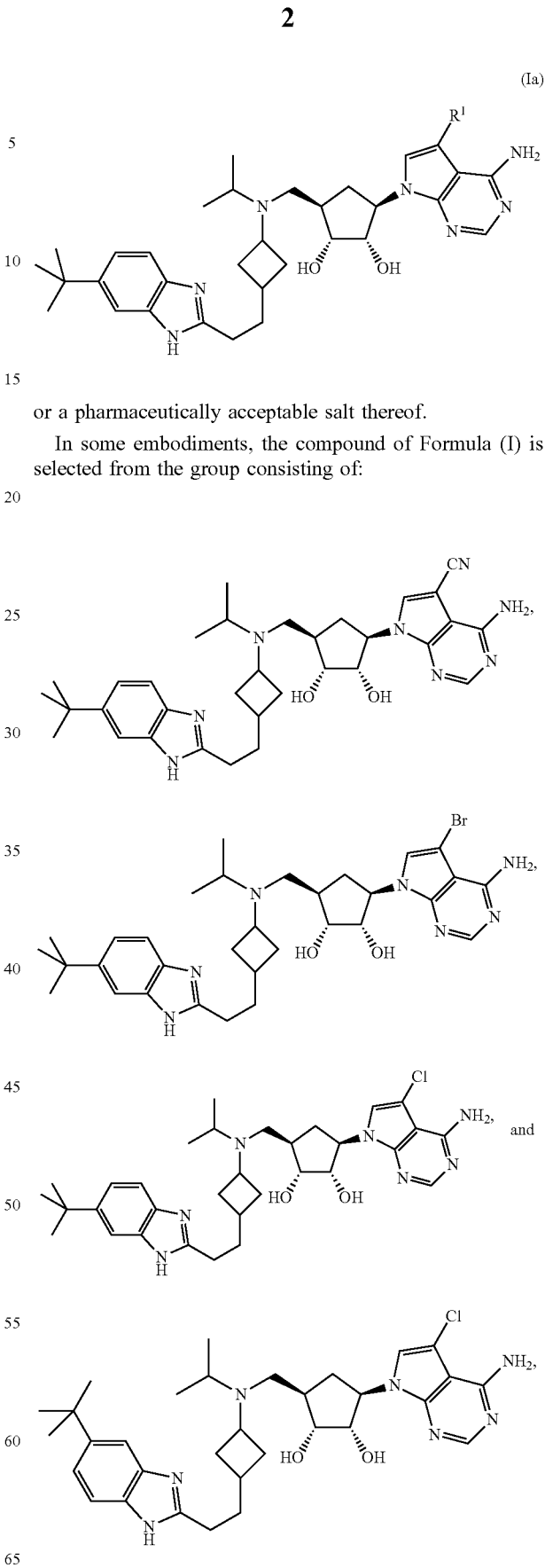

or a pharmaceutically acceptable salt thereof.

In some embodiments, the compound of Formula (I) is selected from the group consisting of:

and or a pharmaceutically acceptable salt thereof.

In some embodiments, the compound of Formula (I) is:

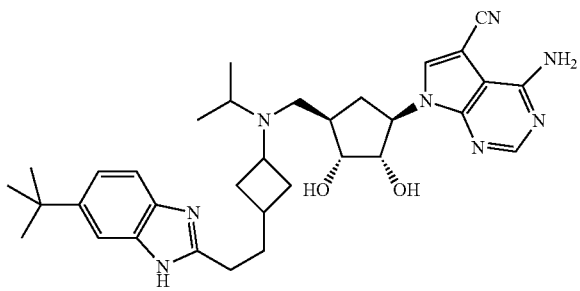 [SMILES: CC(C)N(C[C@H]1C[C@@H](n2cc(C#N)c3c(N)ncnc32)[C@H](O)[C@@H]1O)C1CC(CCc2nc3ccc(C(C)(C)C)cc3[nH]2)C1]

or a pharmaceutically acceptable salt thereof.

In some embodiments, the compound of Formula (I) has a biological half-life of from about 1 h to about 30 h. In some embodiments, the compound of Formula (I) has a biological half-life of from about 10 h to about 30 h. In some embodiments, the compound of Formula (I) has a biological half-life of from about 10 h to about 13 h.

The present disclosure also provides a pharmaceutical composition comprising a compound of Formula (I), or a pharmaceutically acceptable salt thereof, and at least one pharmaceutically acceptable carrier.

The present disclosure also provides methods of modulating an activity of DOT1L, comprising contacting DOT1L with a compound of Formula (I), or a pharmaceutically acceptable salt thereof. In some embodiments, more than one of the compounds of Formula (I) is administered. In some embodiments, modulating an activity of DOT1L comprises inhibiting an activity of the DOT1L.

The present disclosure also provides methods of treating a disease in a patient, wherein the disease is associated with abnormal expression or activity of DOT1L, comprising administering to the patient a therapeutically effective amount of a compound of Formula (I), or a pharmaceutically acceptable salt thereof. In some embodiments, the disease is cancer. In some embodiments, the cancer is a hematological cancer. In some embodiments, the cancer is leukemia. In some embodiments, the leukemia is selected from the group consisting of acute myeloid leukemia, acute lymphocytic leukemia, or mixed lineage leukemia.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Compounds

Figure 1:
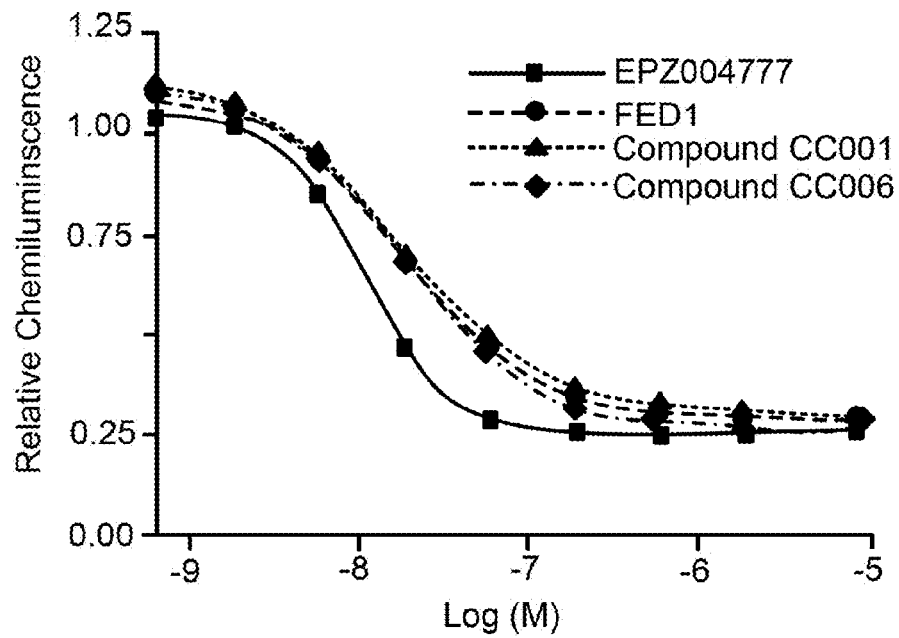
FIG. 1 shows the relative chemiluminescence of the compound of Example 1 (i.e. CC-006) and known DOT1L inhibitors, as determined by fluorescence polarization (FP) assay.

The present application provides, inter alia, a compound of Formula (I):

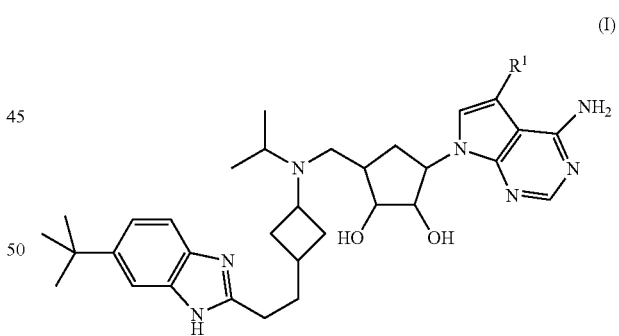

or a pharmaceutically acceptable salt thereof, wherein $R^1$ is selected from the group consisting of CN, halo, and $C_{1-4}$ haloalkyl.

In some embodiments, $R^1$ is halo. In some embodiments, $R^1$ is chloro or bromo. In some embodiments, $R^1$ is chloro. In some embodiments, $R^1$ is bromo.

In some embodiments, $R^1$ is $C_{1-4}$ haloalkyl. In some embodiments, $R^1$ is trifluoromethyl.

In some embodiments, $R^1$ is CN.

In some embodiments, the compound of Formula (I) is a compound of Formula (Ia):

(Ia)

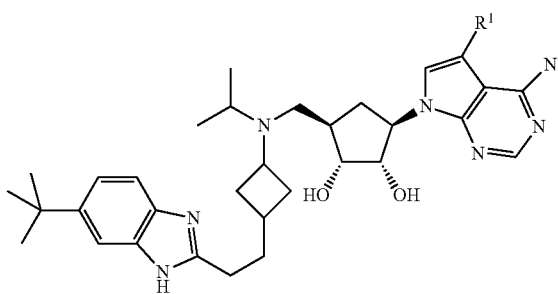

or a pharmaceutically acceptable salt thereof.

In some embodiments, the compound of Formula (I) is selected from the group consisting of:

(CC-006)

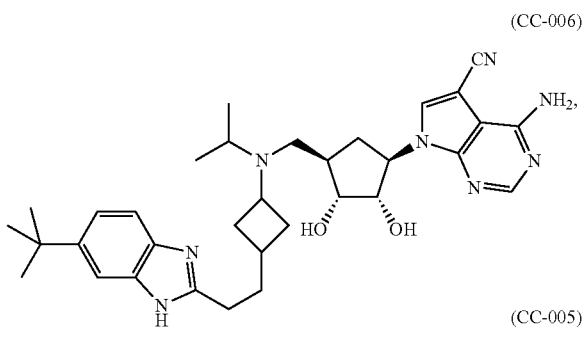 [SMILES: CC(C)N(C[C@H]1C[C@@H](n2cc(C#N)c3c(N)ncnc32)[C@H](O)[C@@H]1O)C1CC(CCc2nc3ccc(C(C)(C)C)cc3[nH]2)C1]

(CC-005)

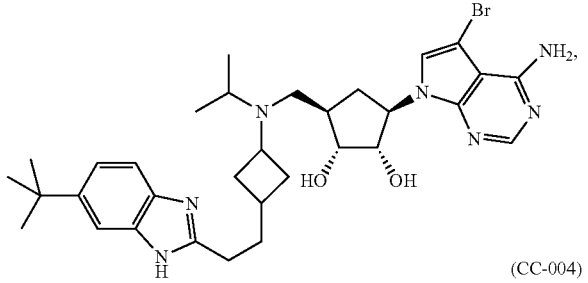

(CC-004)

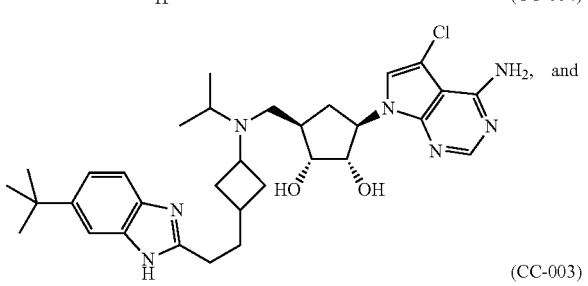

and (CC-003)

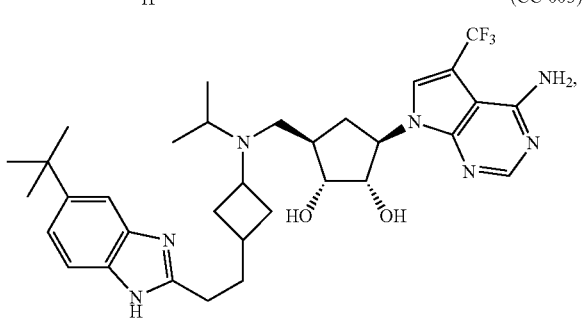

or a pharmaceutically acceptable salt thereof.

In some embodiments, the compound of Formula (I) is:

(CC-006)

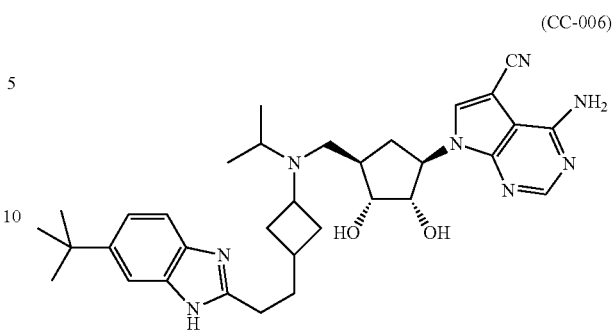

or a pharmaceutically acceptable salt thereof.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "cyano" or "nitrile" refers to a group of Formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo is Cl or Br. In some embodiments, halo is Cl. In some embodiments, halo is Br.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methyl-benzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical Formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The terms, "biological half-life", "half-life", or "$T_{1/2}$" as used herein, refer to the time it takes for the blood-plasma concentration of a compound to halve its steady-state. In some embodiments, the biological half-life is determined by the area under the curve (AUC) of a mean plasma concentration-time profile. In some embodiments, the compounds provided herein have a biological half-life of from about 1 h to about 50 h, for example, from about 1 h to about 40 h, from about 1 h to about 30 h, from about 1 h to about 20 h, from about 1 h to about 15 h, from about 1 h to about 10 h, from about 1 h to about 5 h, from about 5 h to about 40 h, from about 5 h to about 30 h, from about 5 h to about 20 h, from about 5 h to about 15 h, from about 5 h to about 10 h, from about 10 h to about 40 h, from about 10 h to about 30 h, from about 10 h to about 20 h, from about 10 h to about 15 h, or from about 10 h to about 13 h. In some embodiments, the compounds provided herein have a biological half-life of from about 1 h to about 30 h. In some embodiments, the compounds provided herein have a biological half-life of from about 10 h to about 30 h. In some embodiments, the compounds provided herein have a biological half-life of from about 10 h to about 13 h. In some embodiments, the compounds provided herein have a biological half-life of about 12.6 h. It will be appreciated by one of ordinary skill that instrument variation and other factors can affect biological half-life values. Thus, the biological half-life, such as those reported herein, can vary by plus or minus about 0.5 h, and the term "substantially" or "about" as used in the context of biological half-life herein is meant to encompass the above-mentioned variations.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); aq. (aqueous); atm. (atmosphere(s)); ° C. (degrees celcius); calc. (calculated); d (doublet); dd (doublet of doublets); DCM (dichloromethane); DMF (N,N-dimethylformamide); Et (ethyl); EtOAc (ethyl acetate); EtOH (ethanol); g (gram(s)); h (hour(s)); $H_2$ (hydrogen gas); HCl (hydrochloric acid/hydrogen chloride); $H_2O$ (water); HPLC (high performance liquid chromatography); Hz (hertz); $I_2$ (iodine); IPA (isopropyl alcohol); J (coupling constant); $K_2CO_3$ (potassium carbonate); LCMS (liquid chromatography-mass spectrometry); m (multiplet); M (molar); MS (Mass spectrometry); Me (methyl); MeCN (acetonitrile); MeOH (methanol); mg (milligram(s)); $MgSO_4$ (magnesium sulfate); min. (minutes(s)); mL (milliliter(s)); mmol (millimole(s)); $N_2$ (nitrogen gas); NBS (N-bromosuccinimide); NCS (N-chlorosuccinimide); $NaBH_4$ (sodium tetrahydroborate); $NaBH_3CN$ (sodium cyanoborohydride); NaH (sodium hydride); $NH_3$ (ammonia); $NH_4HCO_3$ (ammonium bicarbonate) $NaHCO_3$ (sodium bicarbonate); $NaIO_4$ (sodium periodate); $NaN_3$ (sodium azide); $Na_2SO_4$ (sodium sulfate); $Na_2S_2O_3$ (sodium thiosulfate); NMP (N-methylpyrrolidone); $OsO_4$ (osmium tetroxide); Pd (palladium); Pd/C (palladium on carbon); $Pd(PPh_3)_4$ (tetrakis(triphenylphosphine) palladium(0)); PE (petroleum ether); $PPh_3$ (triphenylphosphine); t (triplet or tertiary); TFA (trifluoroacetic acid); THF (tetrahydrofuran); TLC (thin layer chromatography); μg (microgram(s)); μL (microliter(s)); μM (micromolar); wt % (weight percent); $Zn(CN)_2$ (zinc cyanide).

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in Scheme I. In the process depicted in Scheme I, the acetal-protected carbocycle 2-10 is reacted with 4-chloro-7H-pyrrolo[2,3-d]pyrimidine 2-11 in the presence of a strong base (e.g., sodium hydride) to afford coupled product 2-12. Oxidation of 2-12 (e.g., reaction with sodium periodate and osmium tetroxide) yields aldehyde 2-13, which is subsequently reduced using methods known in the art (e.g., reaction with sodium tetrahydroborate) to the corresponding primary alcohol 2-14. Iodination of alcohol 2-14 affords compound 2-15, and reaction of iodinated compound 2-15 with sodium azide affords 2-16, which is hydrogenated using standard methods known in the art (e.g., reaction with hydrogen gas in the presence of a hydrogenation catalyst) to yield intermediate CC-001-$NH_2$. Coupling of CC-001-$NH_2$ with 1-8 (e.g., in the presence of sodium cyanoborohydride and acetic acid), affords intermediate CC-001-1 (compound 1-8 can be prepared, for example, according to procedures described in U.S. 2014/0051654). Alkylation of the secondary amine moiety (e.g., reaction with 2-iodopropane in the presence of potassium carbonate) yields intermediate CC-001-2. Bromination of CC-001-2 using methods standard in the art (e.g., reaction with N-bromosuccinimide), provides CC-001-3, which is reacted with zinc cyanide in the presence of a palladium catalyst (e.g., $Pd(PPh_3)_4$) to yield the cyano-substituted intermediate CC-001-4. Subsequent acetal-deprotection (e.g., reaction with TFA) affords the compound of Example 1 (i.e. CC-006).

Scheme I

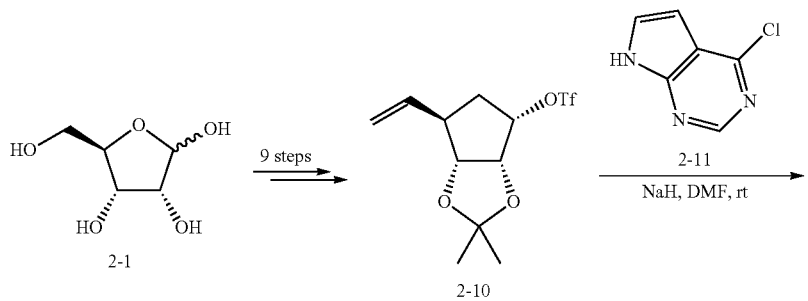

-continued
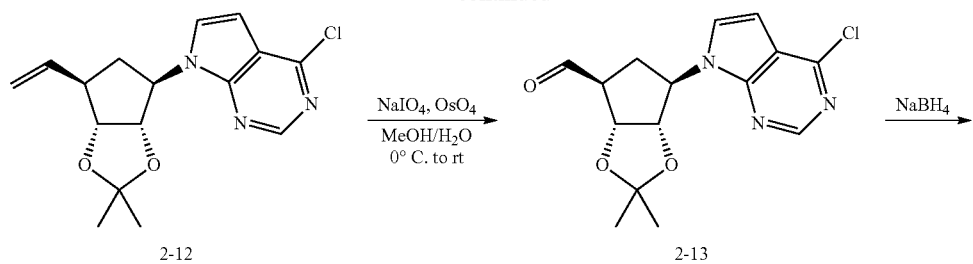
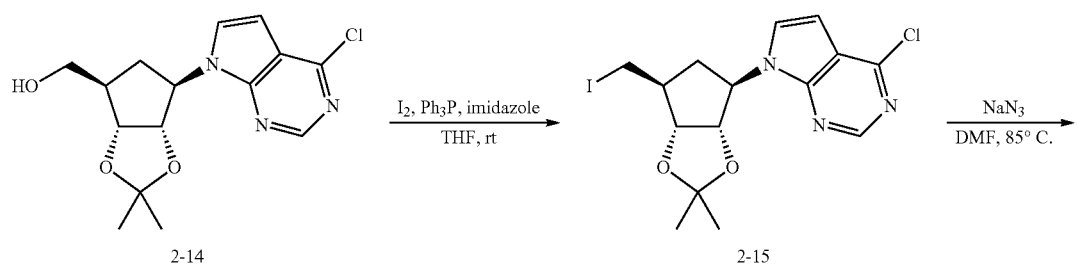
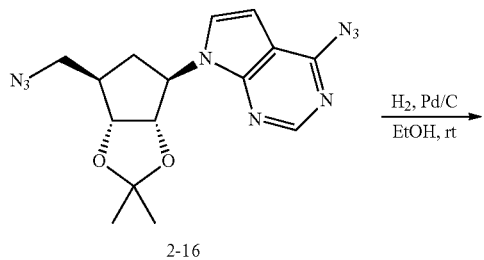
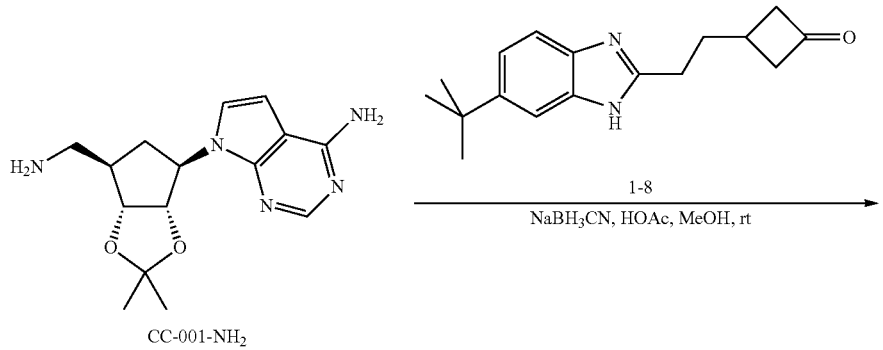
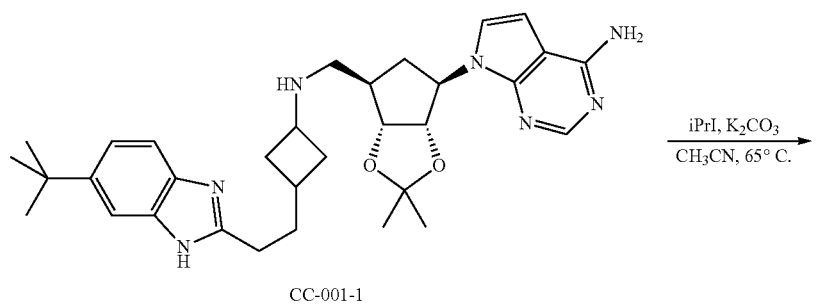

-continued

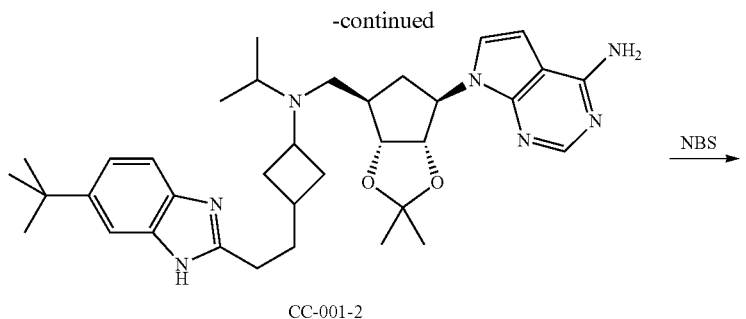

CC-001-2

NBS →

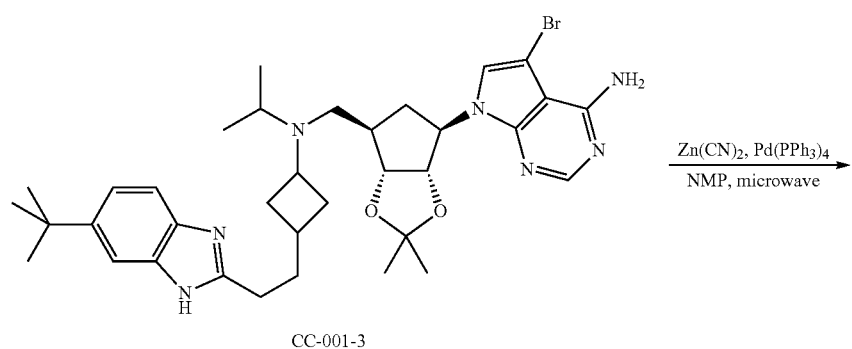

CC-001-3

Zn(CN)₂, Pd(PPh₃)₄
─────────────→
NMP, microwave

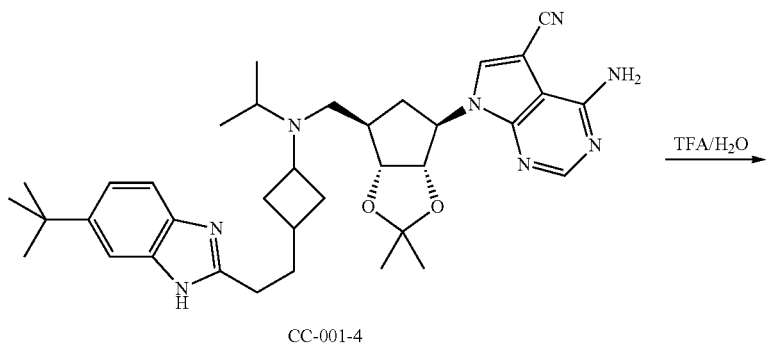

CC-001-4

TFA/H₂O →

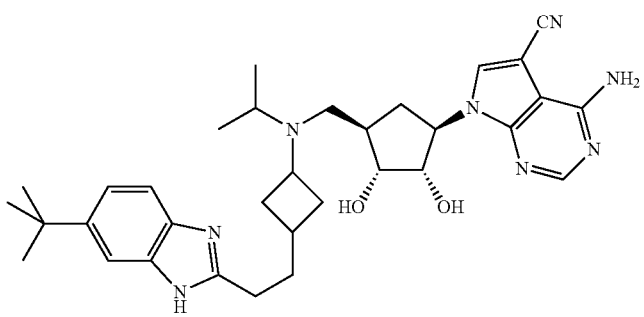

Example 1
(CC-006)

The synthetic method illustrated by Scheme I can also be applied to the synthesis shown below in Scheme II. Chlorination of intermediate CC-001-2 (from Scheme I) using methods known in the art (e.g., reaction with N-chlorosuccinimide) and subsequent acetal-deprotection (e.g., reaction with a strong acid) affords the compound of Example 2 (i.e., CC-004).

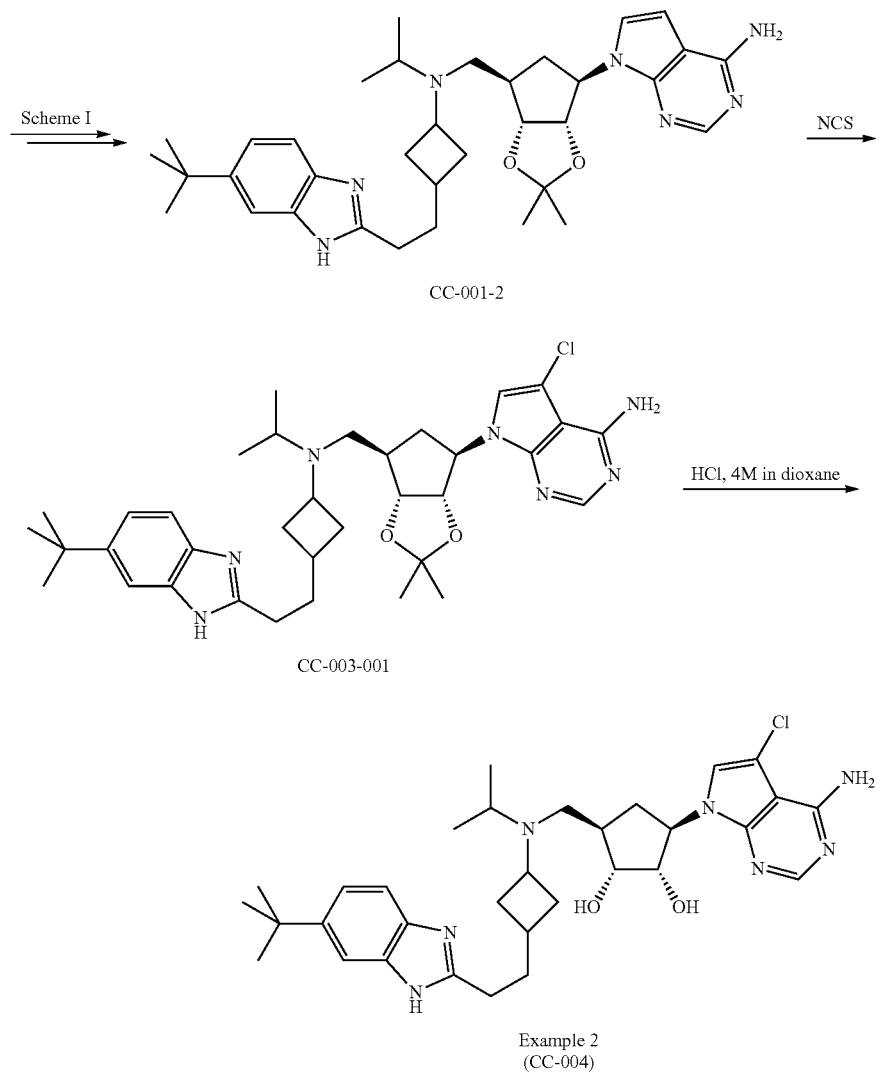
The synthetic method illustrated by Scheme I can also be applied to the synthesis shown below in Scheme III. Acetal-deprotection of intermediate CC-001-3 (from Scheme I) using methods standard in the art (e.g., reaction with a strong acid) affords the compound of Example 3 (i.e., CC-005).
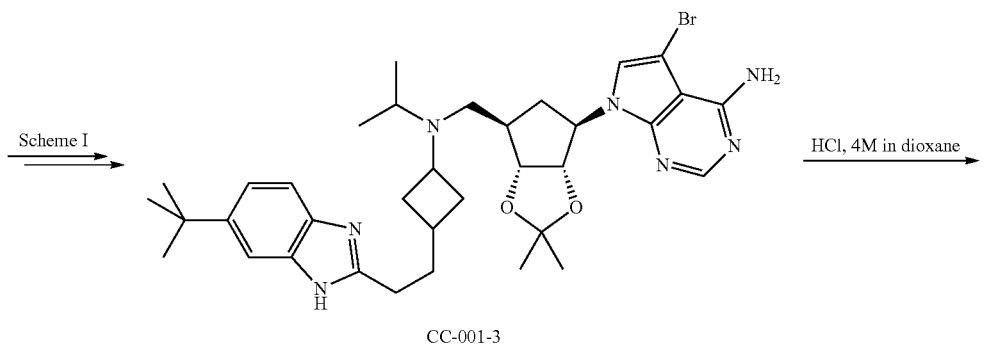

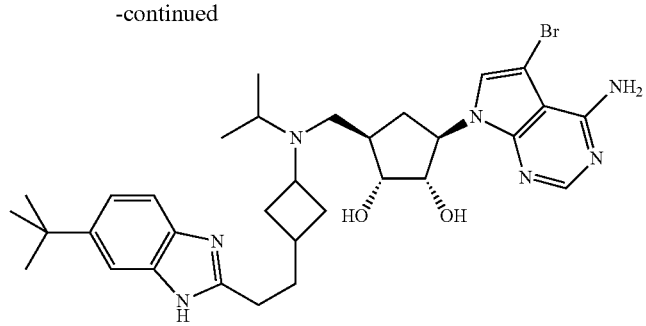

Example 3
(CC-005)

Compounds of Formula (I) can also be prepared, e.g., using a process as illustrated in Scheme IV. In the process depicted in Scheme IV, the acetal-protected carbocycle 2-10 is reacted with 4-chloro-5-(trifluoromethyl)-7H-pyrrolo[2,3-d]pyrimidine (4-11) in the presence of a strong base (e.g., sodium hydride) to afford coupled product 4-12. Oxidation of 4-12 (e.g., reaction with sodium periodate and osmium tetroxide) yields aldehyde 4-13, which is subsequently reduced using methods known in the art (e.g., reaction with sodium tetrahydroborate) to the corresponding primary alcohol 4-14. Iodination of alcohol 4-14 affords compound 4-15, and reaction of iodinated compound 4-15 with sodium azide affords 4-16, which is hydrogenated using standard methods known in the art (e.g., reaction with hydrogen gas in the presence of a hydrogenation catalyst) to yield intermediate CC-003-NH$_2$. Coupling of CC-003-NH$_2$ with 1-8 (e.g., in the presence of sodium cyanoborohydride and acetic acid), affords intermediate CC-003-1 (compound 1-8 can be prepared, for example, according to procedures described in U.S. 2014/0051654). Alkylation of the secondary amine moiety (e.g., reaction with 2-iodopropane in the presence of potassium carbonate) yields intermediate CC-003-2 and subsequent acetal-deprotection (e.g., reaction with TFA) affords the compound of Example 4 (i.e. CC-003).

Scheme IV

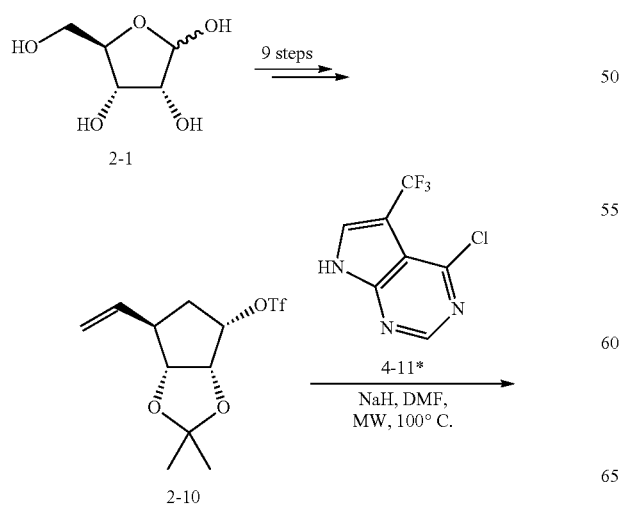

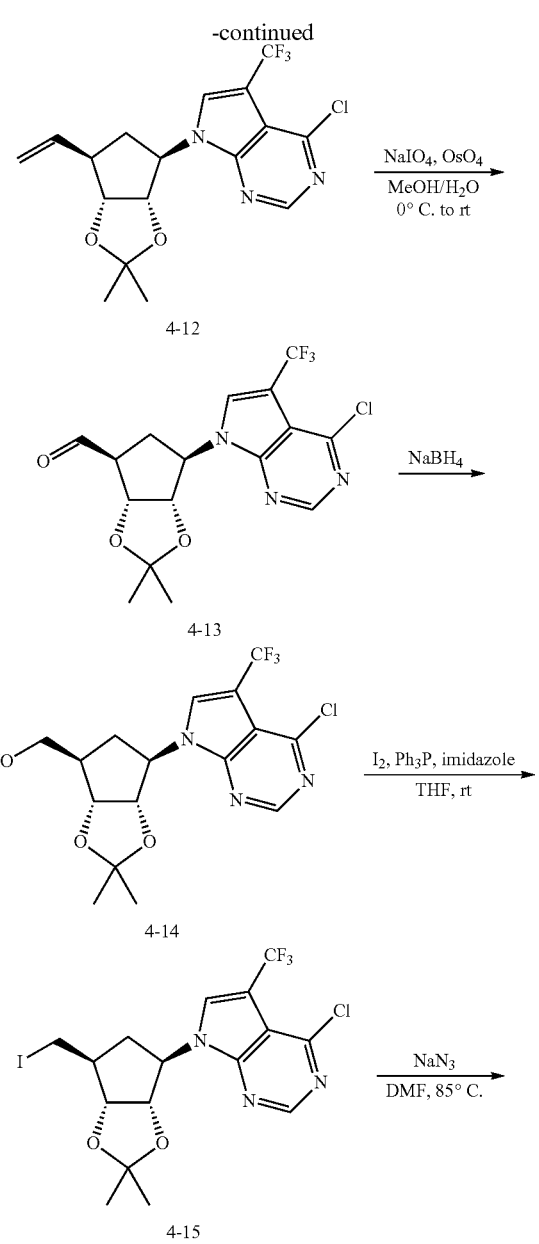

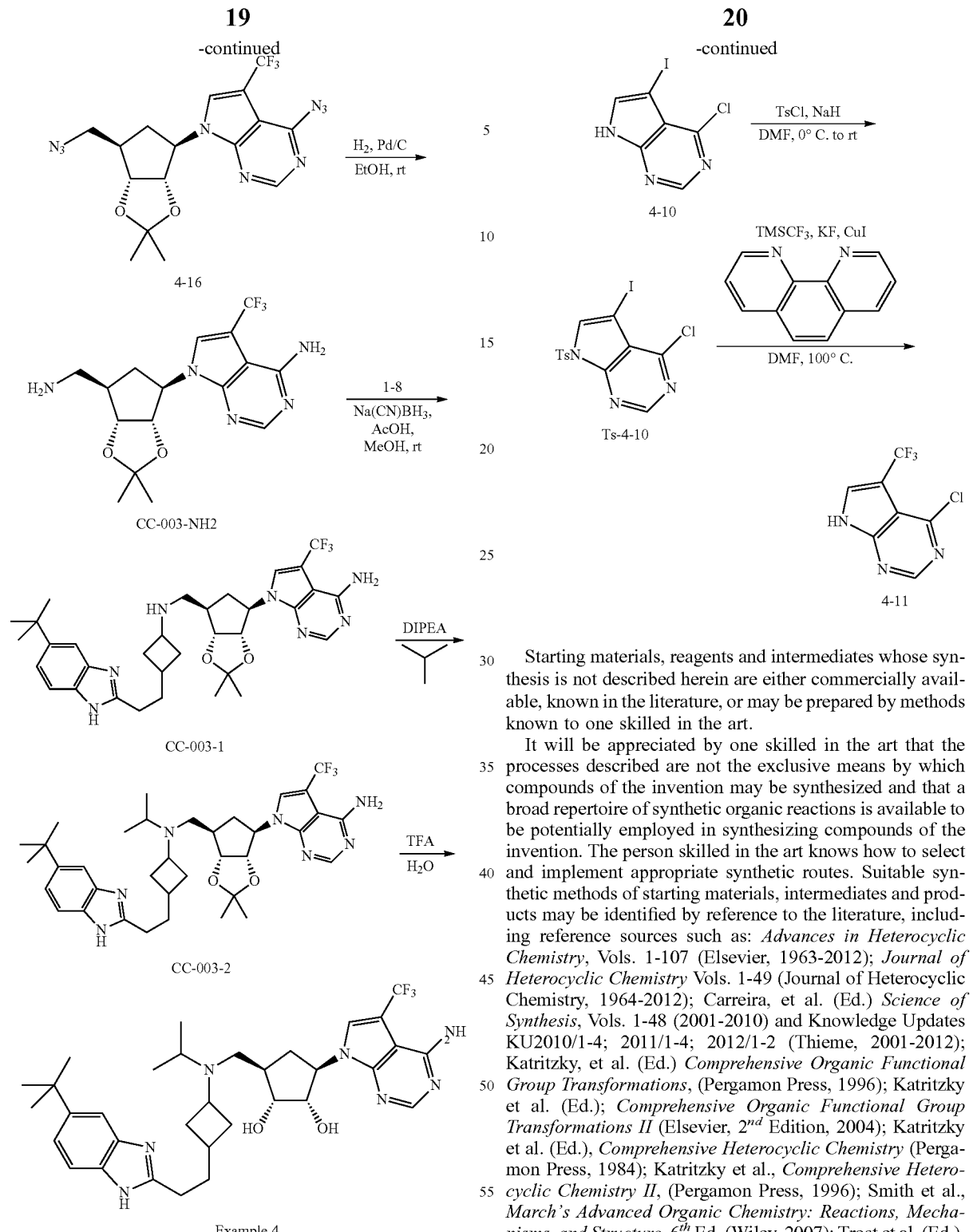

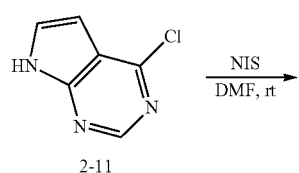

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

Methods

Provided herein are methods of inhibiting DOT1L in a patient. As used herein, the term "patient," refers to any animal, including mammals. For example, mice, rats, other rodents, rabbits, dogs, cats, swine, cattle, sheep, horses, primates, and humans. In some embodiments, the patient is a human or rat. In some embodiments, the patient is a human. The present application further provides methods of modulating an activity of DOT1L, comprising contacting DOT1L with a compound provided herein, or a pharmaceutically acceptable salt thereof. In some embodiments, modulating an activity of DOT1L comprises inhibiting DOT1L. In some embodiments, modulating an activity of DOT1L comprises deregulating the DOT1L. In some embodiments, modulating an activity of DOT1L comprises inhibiting enzymatic activity of DOT1L by occupying SAM binding pocket of DOT1L.

The compounds provided herein can be selective DOT1L inhibitors. As used, the term "selective" means that the compound binds to or inhibits a particular enzyme with greater affinity or potency, respectively, as compared to at least one other enzyme. In some embodiments, selectivity can be at least about, 10-fold, at least about 20-fold, at least about 50-fold, at least about 100-fold, at least about 200-fold, at least about 500-fold or at least about 1000-fold.

Also provided are methods of treating a disease in a patient in need thereof, wherein the disease is associated with DOT1L. In some embodiments, the method comprises administering to the patient a therapeutically effective amount of a DOT1L inhibitor provided herein, or a pharmaceutically acceptable salt thereof, wherein the disease is cancer. In some embodiments, the cancer is a hematological cancer. In some embodiments, the hematological cancer is selected from the group consisting of acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, and germinal center B cell (GCB) diffuse large B cell lymphoma. In some embodiments, the cancer is selected from the group consisting of leukemia, lymphoma, and myeloma. In some embodiments, the cancer is selected from leukemia or lymphoma. In some embodiments, the cancer is leukemia. In some embodiments, the leukemia is selected from the group consisting of acute myeloid leukemia, acute lymphocytic leukemia, or mixed lineage leukemia.

The present application further provides a method of treating cancer in a patient, the method comprising:
(i) determining if the cancer is mediated by DOT1L; and
(ii) if the cancer is determined to be mediated by DOT1L, administering to the patient a therapeutically effective amount of a compound of Formula (I), or a pharmaceutically acceptable salt thereof.

In some embodiments, the cancer is a hematological cancer. In some embodiments, the hematological cancer is selected from the group consisting of acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, and germinal center B cell (GCB) diffuse large B cell lymphoma. In some embodiments, the cancer is selected from the group consisting of leukemia, lymphoma, and myeloma. In some embodiments, the cancer is selected from leukemia or lymphoma. In some embodiments, the cancer is leukemia. In some embodiments, the leukemia is selected from the group consisting of acute myeloid leukemia, acute lymphocytic leukemia, or mixed lineage leukemia.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, or other agents such as therapeutic antibodies, can be used in combination with the compounds of the present application for treatment of DOT1L associated diseases, disorders or conditions. The one or more additional pharmaceutical agents can be administered to a patient simultaneously or sequentially. In some embodiments, more than one of the compounds of Formula (I) is administered.

Example antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20) and antibodies directed to c-MET.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as cortisone, dexamethasone, hydrocortisone, methylprednisolone, prednisolone, and prednisone.

Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example immunosuppressants include azathioprine, chlorambucil, cyclophosphamide, cyclosporine, daclizumab, infliximab, methotrexate, and tacrolimus.

One or more of the following agents may be used in combination with the compounds provided herein and are presented as a non-limiting list: a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Sml1, triapine, didox, trimidox, amidox, 3-AP, MDL-101,731, bendamustine, ofatumumab, and GS-1101 (also known as CAL-101).

Pharmaceutical Formulations and Dosage Forms

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, Formulation of the excipient, and its route of administration. Effective doses can be extrapolated from dose-response curves derived from in vitro or animal model test systems.

EXAMPLES

General Methods

Reactions were run as described in the individual procedures using standard double manifold and syringe techniques; glassware was dried by baking in an oven at 130° C. for 12 h prior to use. Solvents were purchased anhydrous from Sigma-Aldrich and used as received, except EtOH, which was stored over 4 Å molecular sieves. HPLC grade solvents were used for aqueous work-ups and chromatography. Reagents were used as received.

Reactions were monitored by thin-layer chromatography using EMD silica gel 60 F254 (250-micron) glass-backed plates (visualized by UV fluorescence quenching and staining with KMnO4) and by LC-MS using a Waters Aquity BEH C18 2×50 mm 1.7 µm particle column (50° C.) eluting at 1 mL/min with $H_2O$/acetonitrile (0.2% v/v added formic acid or concentrated $NH_4OH$(aq.) solution; 95:5(0 min)→1:99(3.60 min)→1:99(4.00 min)) using alternating positive/negative electrospray ionization (125-1000 amu) and UV detection (210-350 nm). Flash column chromatography was carried out using Merck grade 9385 silica gel 60 Å pore size (230-400 mesh). Melting points were obtained using a capillary melting point apparatus and are uncorrected.

$^1H$ NMR spectra were recorded at 400 MHz on a Bruker spectrometer and are reported in ppm using the residual solvent signal (dimethylsulfoxide-d6=2.50 ppm; chloroform-d=7.27 ppm; methanol-d4=3.31 ppm; dichloromethane-d2=5.32 ppm) as an internal standard. Data are reported as: {(δ shift), [(s=singlet, d=doublet, dd, doublet of doublets, ddd=doublet of a dd, t=triplet, quin=quintet, sept=septet, br=broad, ap=apparent), (J=coupling constant in Hz) and (integration)]}. Proton-decoupled $^{13}C$ NMR specta were recorded at 100 MHz on a Bruker spectrometer and are reported in ppm using the residual solvent signal (chloroform-d=77.0 ppm; dimethylsulfoxide-d6=39.51 ppm; methanol-d4=49.15 ppm) as an internal standard. Infrared spectra were recorded using an ATR-FTIR instrument. High resolution mass spectra were acquired by flow injection on a qTOF Premiere Mass Spectrometer operating in ES+ ionization with resolution ~15,000.

Example 1

4-amino-7-((1R,2S,3R,4R)-4-(((3-(2-(6-(tert-butyl)-1H-benzo[d]imidazol-2-yl)ethyl)cyclobutyl)(isopropyl)amino)methyl)-2,3-dihydroxycyclopentyl)-7H-pyrrolo[2,3-d]pyrimidine-5-carbonitrile (CC-006)

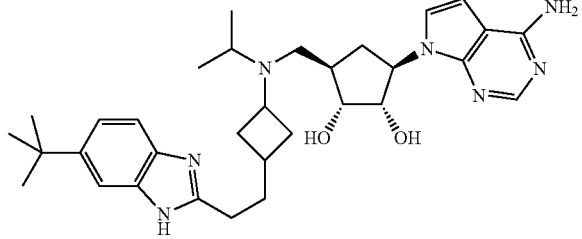

Step 1. 4-chloro-7-((3aS,4R,6R,6aR)-2,2-dimethyl-6-vinyltetrahydro-3aH-cyclopenta[d][1,3]dioxol-4-yl)-7H-pyrrolo[2,3-d]pyrimidine

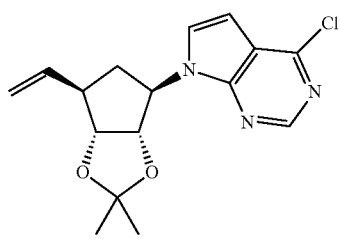

2-12

To a suspension of NaH (78.0 mg, 60% dispersion in mineral oil, 3.25 mmol) in anhydrous DMF (2 mL) was added a solution of 4-chloro-7H-pyrrolo[2,3-d]pyrimidine (2-1) (491 mg, 3.20 mmol) in DMF (2 mL) via syringe dropwise at 0° C. The resulting clear solution was stirred at 0° C. for 15 min and a previously prepared solution of (3aR,4S,6R,6aR)-2,2-dimethyl-6-vinyltetrahydro-3aH-cyclopenta[d][1,3]dioxol-4-yl trifluoromethanesulfonate (2-10) (8.00 mL, 2.00 mmol theoretical) in DMF (3 ml) was added. After the addition, the reaction mixture was warmed to room temperature and stirred overnight. The reaction mixture was quenched by the addition of H₂O at 0° C. and extracted with EtOAc (3×50 mL). The combined organic phases were dried over anhydrous MgSO₄, filtered, concentrated in vacuo, and the residue was purified by silica gel chromatography (EtOAc/hexanes: 1/10) to give 2-12 as a white solid. MS: m/z (M+1)⁺: 320.1.

Step 2. (3aR,4S,6R,6aS)-6-(4-chloro-7H-pyrrolo[2,3-d]pyrimidin-7-yl)-2,2-dimethyltetrahydro-3aH-cyclopenta[d][1,3]dioxole-4-carbaldehyde

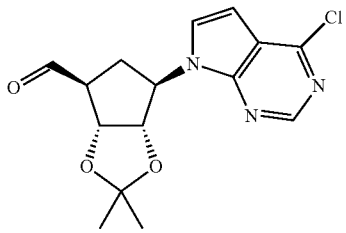

2-13

To a solution of 2-12 in MeOH (35 mL) and H₂O (18 mL) was added NaIO₄ (4.33 g, 20.2 mmol). The mixture was cooled to 0° C. and OsO₄ (30 mg) was added. The reaction was stirred at 0° C. for 1 h and then at room temperature for 2 h. The formed white solid was removed by filtration, and the filtrate was concentrated in vacuo at ambient temperature. The residue was redissolved in DCM (200 mL), and the organic solution was washed with H₂O (30 mL) and brine (30 mL) and dried over anhydrous MgSO₄. After filtration, DCM was removed in vacuo at ambient temperature to give the crude product 2-13 as yellow oil. MS: m/z (M+1)⁺: 321.8.

Step 3. ((3aR,4R,6R,6aS)-6-(4-chloro-7H-pyrrolo[2,3-d]pyrimidin-7-yl)-2,2-dimethyltetrahydro-3aH-cyclopenta[d][1,3]dioxol-4-yl)methanol

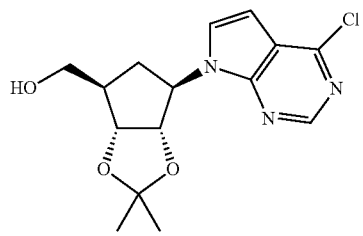

2-14

To a solution of 2-13 in MeOH (40 mL) was added NaBH₄ (1.2 g, 30.8 mmol) portionwise at 0° C. After the reaction was stirred 0° C. for 1 h, the solvent was removed in vacuo, and DCM (150 mL) and H₂O (30 mL) were added. The organic layer was washed with brine (30 mL), dried over anhydrous MgSO₄, filtered, and concentrated to dryness in vacuo. The residue was purified by short silica gel column chromatography (beginning with EtOAc:hexanes, 1:2, and then EtOAc) to give 2-14 as a white solid. MS: m/z (M+1)⁺: 324.0.

Step 4. 4-chloro-7-((3aS,4R,6S,6aR)-6-(iodomethyl)-2,2-dimethyltetrahydro-3aH-cyclopenta[d][1,3]dioxol-4-yl)-7H-pyrrolo[2,3-d]pyrimidine

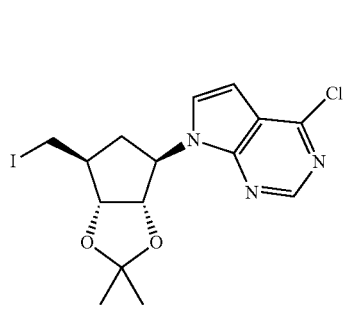

2-15

To a solution of PPh$_3$ (226 mg, 0.862 mmol) and imidazole (61.2 mg, 0.899 mmol) in anhydrous THF (10 mL) was added 12 (218 mg, 0.859 mmol) at room temperature. The resulting yellow-orange mixture was stirred for 15 min, then alcohol 2-14 (139 mg, 0.427 mmol) was added as a solution in THF (2 mL) over 2-3 minutes via syringe and the resulting mixture was stirred for 1 h. When the reaction was complete, it was quenched by the addition of saturated Na$_2$S$_2$O$_3$ (30 mL). The mixture was then extracted with DCM (3×20 mL). The organic phases were dried over anhydrous MgSO$_4$, filtered, concentrated in vacuo, and the residue was purified by silica gel chromatography (PE/EA: 4/1) to give 2-15 as yellow oil. MS: m/z (M+1)$^+$: 433.9.

Step 5. 4-azido-7-((3aS,4R,6R,6aR)-6-(azidomethyl)-2,2-dimethyltetrahydro-3aH-cyclopenta[d][1,3]dioxol-4-yl)-7H-pyrrolo[2,3-d]pyrimidine

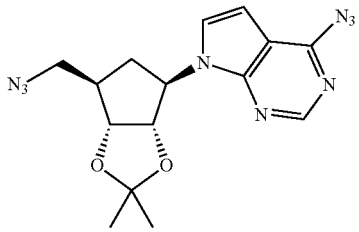

2-16

A mixture of 2-15 (122 mg, 0.280 mmol) and NaN$_3$ (46.0 mg, 0.7 mmol) in DMF (1.5 mL) was stirred and heated at 85° C. for 5 h. The mixture was cooled to room temperature, diluted with EtOAc (15 mL), washed with H$_2$O (3×5 mL) and brine (1×10 mL), dried over anhydrous MgSO$_4$, and filtered. The filtrate was concentrated in vacuo to give 101 mg of 2-16. MS: m/z (M+1)$^+$: 356.1.

Step 6. 7-((3aS,4R,6R,6aR)-6-(aminomethyl)-2,2-dimethyltetrahydro-3aH-cyclopenta[d][1,3]dioxol-4-yl)-7H-pyrrolo[2,3-d]pyrimidin-4-amine

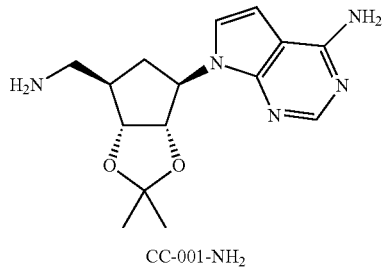 [SMILES: CC1(C)O[C@@H]2[C@@H](CN)C[C@@H](n3ccc4c(N)ncnc43)[C@@H]2O1]

CC-001-NH$_2$

To a 50 ml, round-bottomed flask were added 2-16 (95.4 mg, 0.267 mmol), Pd/C (8.5 mg, 10% w/w on activated carbon, 0.80 mmol, 30 mol %) and EtOH (5 mL). The flask was purged with H$_2$ several times, and the mixture was stirred at room temperature for 2 h. The mixture was filtered through a pad (2×2 cm) of Celite. The filter cake was washed with MeOH (2×5 mL) and the filtrate was concentrated in vacuo to give 98.4 mg of CC-001-NH$_2$ as slightly cloudy oil. MS: m/z (M+1)$^+$: 304.1.

Step 7. 7-((3aS,4R,6R,6aR)-6-(((3-(2-(6-(tert-butyl)-1H-benzo[d]imidazol-2-yl)ethyl)cyclobutyl)amino)methyl)-2,2-dimethyltetrahydro-3aH-cyclopenta[d][1,3]dioxol-4-yl)-7H-pyrrolo[2,3-d]pyrimidin-4-amine

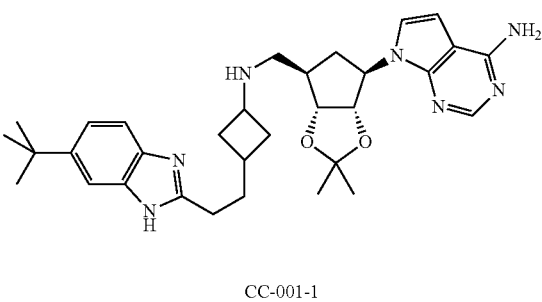 [SMILES: CC1(C)O[C@@H]2[C@@H](CNC3CC(CCc4nc5ccc(C(C)(C)C)cc5[nH]4)C3)C[C@@H](n3ccc4c(N)ncnc43)[C@@H]2O1]

CC-001-1

To a solution of CC-001-NH$_2$ (50 mg, 0.16 mmol) in 3 mL of MeOH was added NaBH$_3$CN (21 mg, 0.33 mmol). The reaction mixture was adjusted to pH=6 with 10% AcOH in MeOH, and then 3-(2-(6-(tert-butyl)-1H-benzo[d]imidazol-2-yl)ethyl)cyclobutanone (45 mg, 0.16 mmol, see U.S. 2014/0051654) was added. The mixture was stirred at room temperature for 16 h, and then saturated NaHCO$_3$ solution (2 mL) and H$_2$O (5 mL) were added. The resulting mixture was stirred at room temperature for an additional 30 min, and then extracted with DCM (40 mL). The organic phase was dried over anhydrous MgSO$_4$ and concentrated in vacuo to afford the crude product, which was purified by washing with EtOAc:hexanes, 1:5, to give CC-001-1 (30 mg) as a white solid. MS: m/z (M+1)$^+$: 588.2.

Step 8. 7-((3aS,4R,6R,6aR)-6-(((3-(2-(6-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-7H-pyrrolo[2,3-d]pyrimidin-4-amine

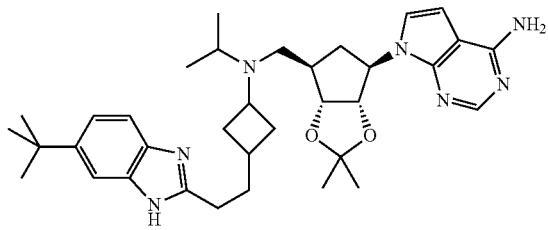

CC-001-2

To a mixture of CC-001-1 (50 mg, 0.09 mmol) and K$_2$CO$_3$ (38 mg, 0.27 mmol) in MeCN (5 ml) was added 2-iodopropane (46 mg, 0.27 mmol). The mixture was stirred at 80° C. for 72 h, cooled to room temperature, and filtered to remove the solid. The filtrate was concentrated in vacuo, and the residue was purified by silica gel chromatography (DCM:MeOH, 15:1, with the addition of NH$_3$.H$_2$O) to afford CC-001-2 (25 mg) as a white solid. MS: m/z (M+1)$^+$: 600.0.

Step 9. 5-bromo-7-((3aS,4R,6R,6aR)-6-(((3-(2-(6-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-7H-pyrrolo[2,3-d]pyrimidin-4-amine

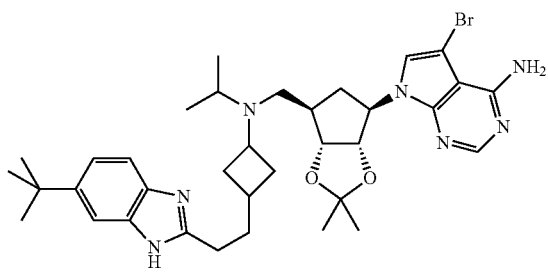

CC-001-3

To a solution of CC-001-2 (100 mg, 0.17 mmol) in 5 mL of DMF was added NBS (30 mg, 0.17 mmol). The mixture was stirred at room temperature for 3 h, and then poured into 50 mL of H$_2$O and extracted with DCM (3×30 mL). The organic phase was dried over anhydrous MgSO$_4$, filtered, and the filtrate was concentrated in vacuo to afford the crude product, which was purified by prep-HPLC to afford CC-001-3 (20 mg) and 40 mg of CC-001-2. MS: m/z (M+1)$^+$: 678.3.

Step 10. 4-amino-7-((3aS,4R,6R,6aR)-6-(((3-(2-(6-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-7H-pyrrolo[2,3-d]pyrimidine-5-carbonitrile

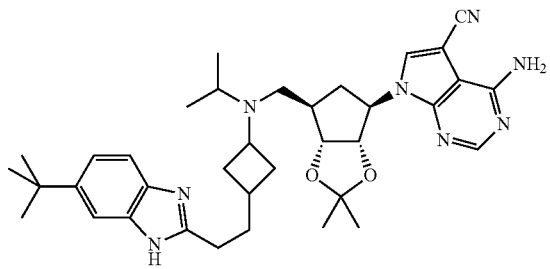

CC-001-4

To a solution of CC-001-3 (3 mg, 0.0044 mmol) in 2 mL of NMP were added Zn(CN)$_2$ (1 mg, 0.0088 mmol) and Pd(PPh$_3$)$_4$ (5 mg, 0.0044 mmol) under N$_2$. The mixture was stirred and heated at 160° C. for 1 h in a microwave synthesizer (CEM Corporation). The mixture was filtered and the filtrate was purified by prep-HPLC to afford the pure product CC-001-4 (1.5 mg) as a white solid. MS: m/z (M+1)$^+$: 625.0.

Step 11. 4-amino-7-((1R,2S,3R,4R)-4-(((3-(2-(6-(tert-butyl)-1H-benzo[d]imidazol-2-yl)ethyl)cyclobutyl)(isopropyl)amino)methyl)-2,3-dihydroxycyclopentyl)-7H-pyrrolo[2,3-d]pyrimidine-5-carbonitrile To an ice cold mixture of TFA (1 mL) and water (0.2 mL) was added CC-001-4 (3 mg, 0.0048 mmol). The solution was stirred at 0° C. for 30 min, and then warmed to room temperature and stirred for 3 h. LC-MS indicated the reaction was complete. The mixture was concentrated in vacuo, and the residue was taken up in DCM (5 mL) and the pH was adjusted with saturated NaHCO$_3$ to pH~8. The organic phase was separated and the aqueous phase was extracted with DCM (1×1 mL). The combined organic phases were dried over anhydrous Na$_2$SO$_4$, filtered and concentrated in vacuo. The residue was purified by prep-HPLC (MeCN/NH$_4$HCO$_3$) to afford the title compound as a white solid (1.7 mg). MS: m/z (M+1)$^+$: 584.9.

Example 2

(1R,2S,3R,5R)-3-(4-amino-5-chloro-7H-pyrrolo[2,3-d]pyrimidin-7-yl)-5-(((3-(2-(6-(tert-butyl)-1H-benzo[d]imidazol-2-yl)ethyl)cyclobutyl)(isopropyl)amino)methyl)cyclopentane-1,2-diol (CC-004)

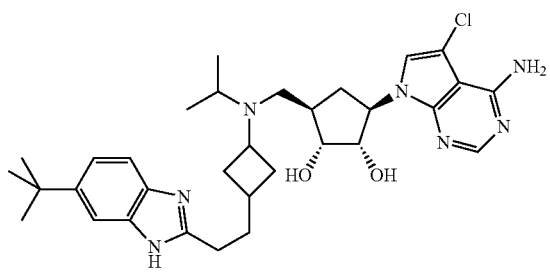 [SMILES: CC(C)N(C[C@H]1C[C@@H](n2cc(Cl)c3c(N)ncnc32)[C@H](O)[C@@H]1O)C1CC(CCc2nc3ccc(C(C)(C)C)cc3[nH]2)C1]

Step 1. 7-((3aS,4R,6R,6aR)-6-(((3-(2-(6-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-5-chloro-7H-pyrrolo[2,3-d]pyrimidin-4-amine Example 4

(1R,2S,3R,5R)-3-(4-amino-5-(trifluoromethyl)-7H-pyrrolo[2,3-d]pyrimidin-7-yl)-5-(((3-(2-(5-(tert-butyl)-1H-benzo[d]imidazol-2-yl)ethyl)cyclobutyl)(isopropyl)amino)methyl)cyclopentane-1,2-diol (CC-003)

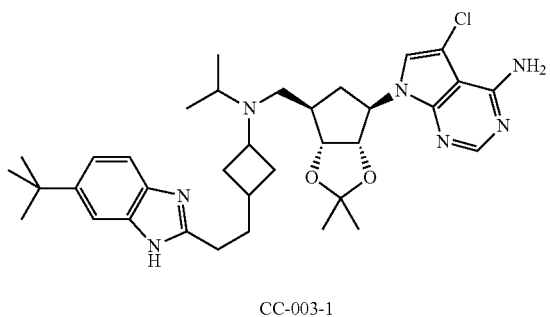 [SMILES: CC(C)N(C[C@H]1C[C@@H](n2cc(Cl)c3c(N)ncnc32)[C@@H]2OC(C)(C)O[C@H]12)C1CC(CCc2nc3ccc(C(C)(C)C)cc3[nH]2)C1]

CC-003-1

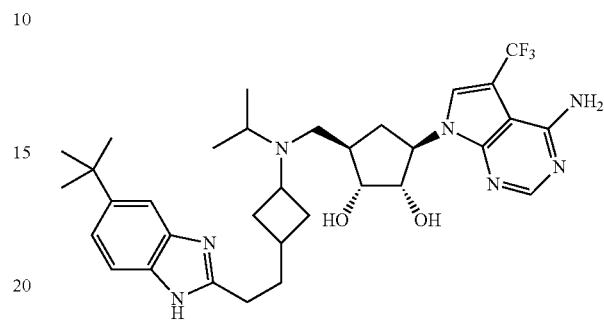

The sub-title compound (CC-003-1) can be prepared according to the procedure provided in Scheme II, e.g., by reaction of intermediate CC-001-2 with N-chlorosuccinimide using methods that are standard in the art.

The title compound can be prepared according to the procedure provided in Scheme IV, (i.e., a method analogous to Example 1, Steps 1-8 and 11), by substituting intermediate 4-11 for intermediate 2-11. LCMS retention time, 1.79 min, MS, 627.8.

Step 2. (1R,2S,3R,5R)-3-(4-amino-5-chloro-7H-pyrrolo[2,3-d]pyrimidin-7-yl)-5-(((3-(2-(6-(tert-butyl)-1H-benzo[d]imidazol-2-yl)ethyl)cyclobutyl)(isopropyl)amino)methyl)cyclopentane-1,2-diol The title product can be prepared, e.g., by reacting the acetal-protected intermediate CC-003-1 (from Step 1) in the presence of a strong acid (e.g., hydrochloric acid). LCMS retention time: 1.81 min; MS, 581.3

Example 3

(1R,2S,3R,5R)-3-(4-amino-5-bromo-7H-pyrrolo[2,3-d]pyrimidin-7-yl)-5-(((3-(2-(6-(tert-butyl)-1H-benzo[d]imidazol-2-yl)ethyl)cyclobutyl)(isopropyl)amino)methyl)cyclopentane-1,2-diol (CC-005)

Example 5

Fluorescence Polarization Assay

This assay can be carried out in a suitable buffer (e.g., phosphate buffered saline, pH 7.4, 1 mM DTT). DOT1L or an active fragment thereof can be used (e.g., DOT1L SET domain) can be used, and FED1-FITC (shown below) can be used as the probe. The protein (10 μM for compound screening) is dissolved in the buffer to the desired concentration. In a multi-well plate, 5 μL of protein solution is added to each well and 5 μL FED1-FITC solution (10 nM) is added to each well with or without a test compound. The plate is spun and then incubated at room temperature in the dark for 30 minutes. The results of a representative FP assay are shown in FIG. 1.

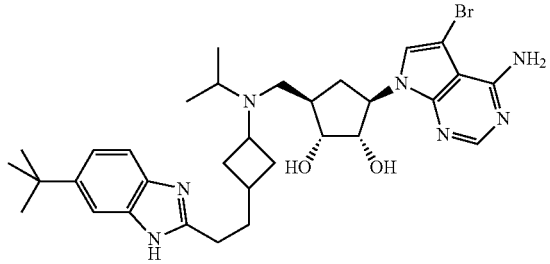 [SMILES: CC(C)N(C[C@H]1C[C@@H](n2cc(Br)c3c(N)ncnc32)[C@H](O)[C@@H]1O)C1CC(CCc2nc3ccc(C(C)(C)C)cc3[nH]2)C1]

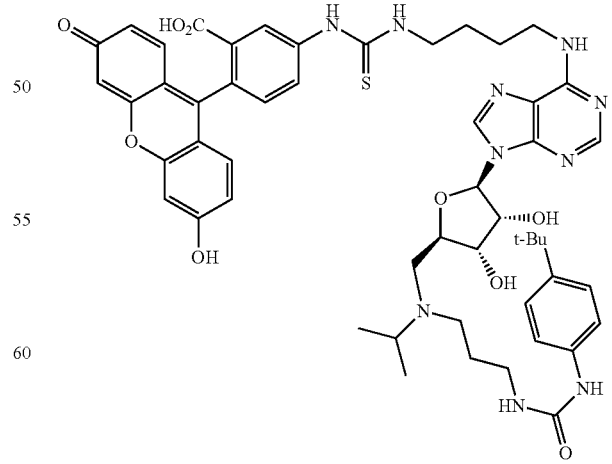

FED1-FITC Probe

The title product can be prepared according to the procedure provided in Scheme III, e.g., by reacting intermediate CC-001-3 (from Example 1, Step 9) in the presence of a strong acid (e.g., hydrochloric acid). LCMS retention time 2.06, MS, 638.3

Example 6

Differential Scanning Fluorimetry (DFS) Assay

Figure 2:
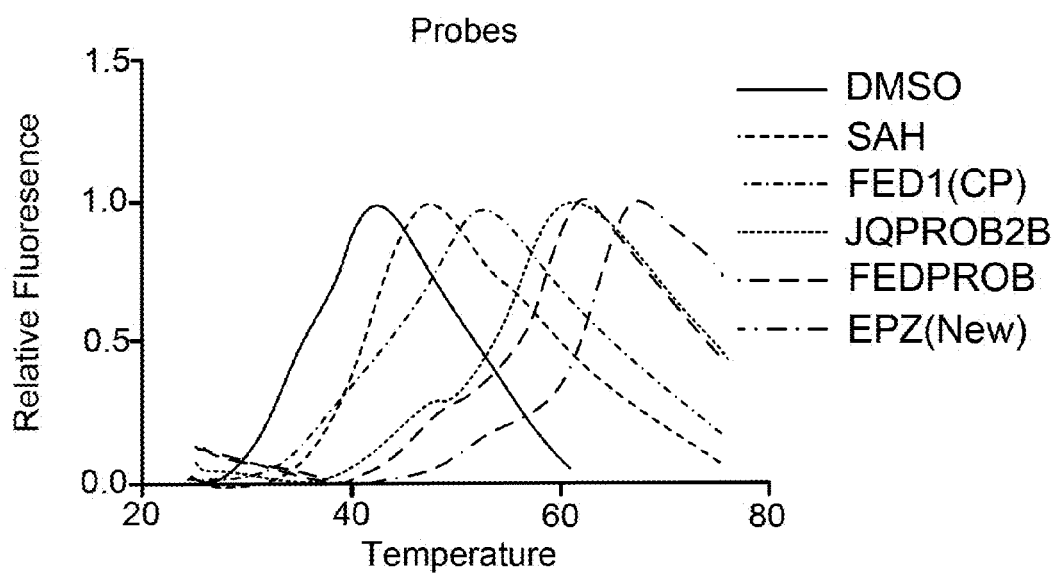
FIG. 2 shows the results of a Differential Scanning Fluorimetry (DSF) Assay.

In this assay, the effect of a small molecule on protein stability is used to assess binding of the small molecule to the protein. Generally, specific binding will stabilize the protein. The results of one such assay are shown in FIG. 2 (bind effect of S-adenosylhomocysteine (SAH), EPZ004777 (see U.S. 2014/0051654), and FEDPROB are shown).

Example 7

Amplified Luminescent Proximity Homogeneous Assay Development (ALPHA Assay)

In and ALPHA assay binding of binding partners captured on the beads leads to an energy transfer from one bead to the other, ultimately producing a luminescent signal. Alpha assays require two bead types: donor beads and acceptor beads. Donor beads contain a photosensitizer, phthalocyanine, which converts ambient oxygen to an excited and reactive form of $O_2$, singlet oxygen, upon illumination at 680 nm. Within its 4 μsec half-life, singlet oxygen can diffuse approximately 200 nm in solution. If an Acceptor bead is within that distance, energy is transferred from the singlet oxygen to thioxene derivatives within the Acceptor bead, resulting in light production. If the Donor bead is not in proximity of an Acceptor bead, the singlet oxygen falls to ground state and no signal is produced.

Figure 3:
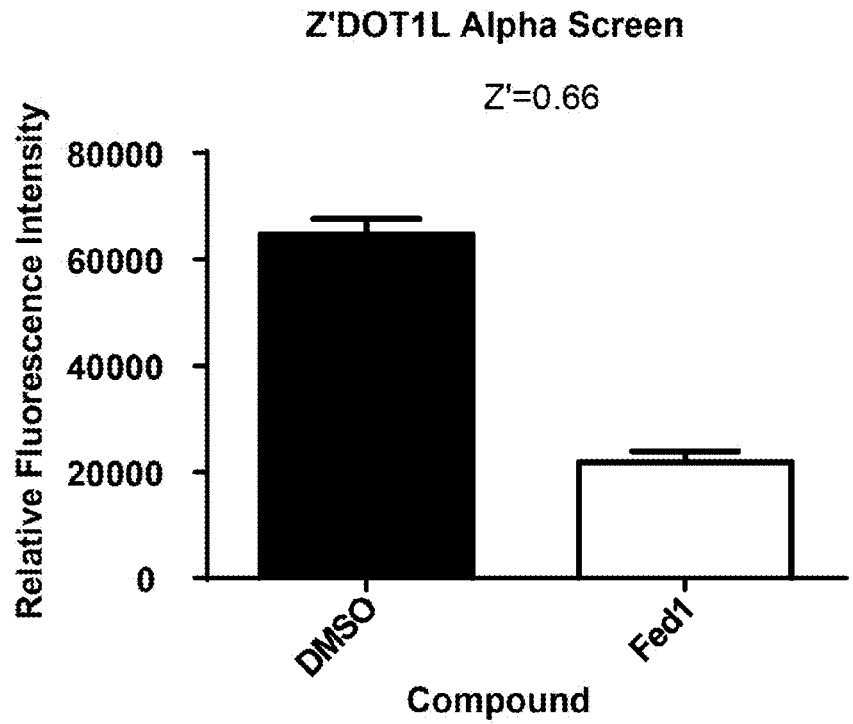
FIG. 3 shows the results of an Amplified Luminescent Proximity Homogeneous Assay Development (ALPHA) assay.
Figure 9:
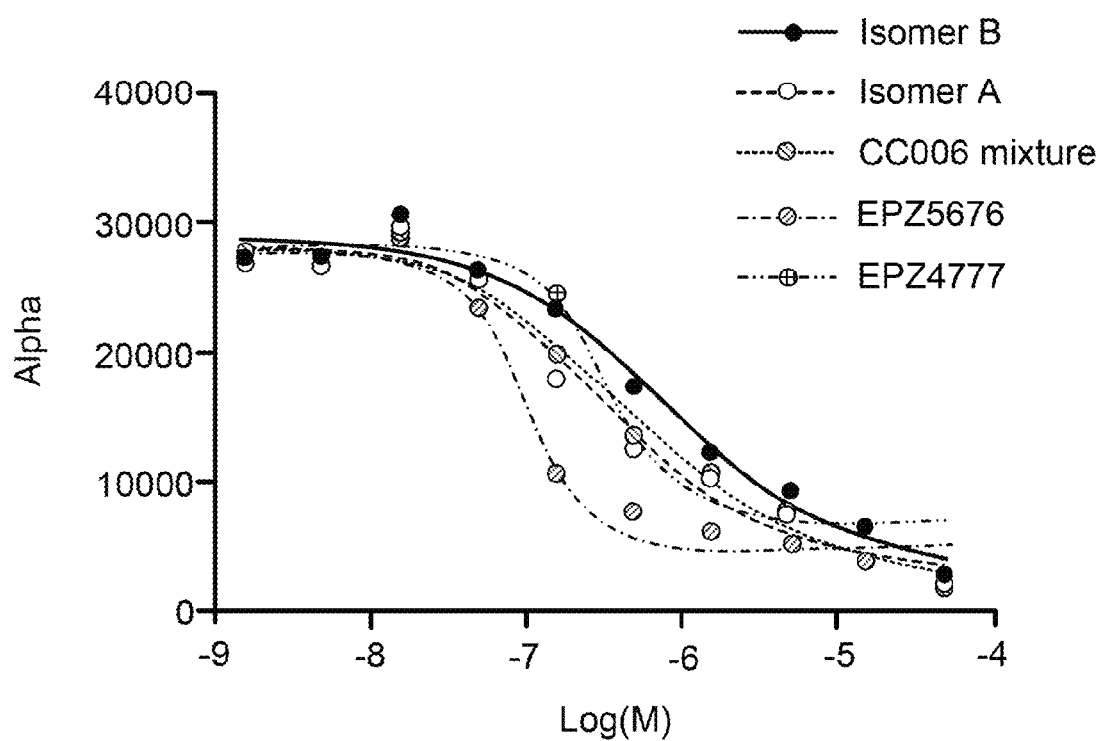
FIG. 9 shows representative data from a biochemical assay (ALPHA screen). The data shows that the compound of Example 1 (i.e. CC-006) binds to DOT1L.
Figure 10B:
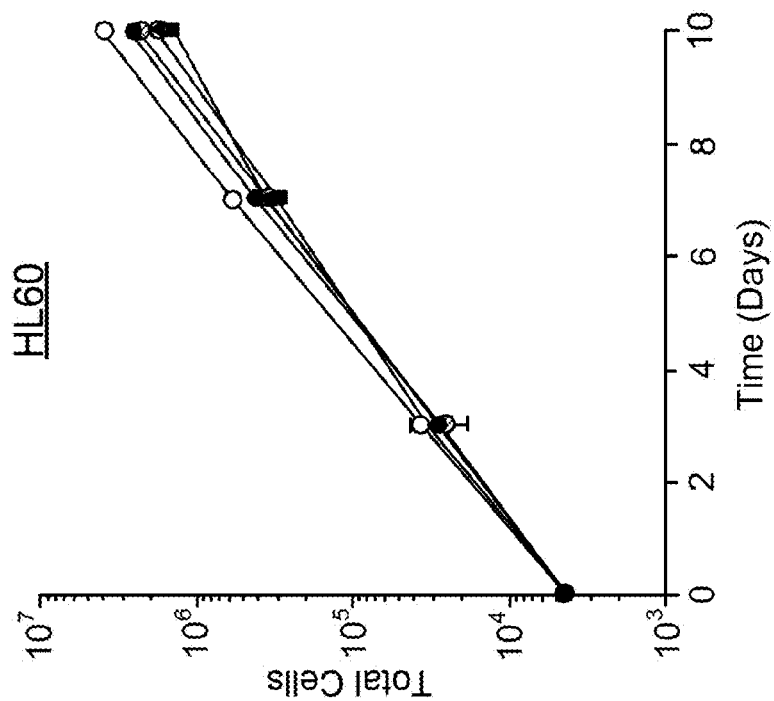
FIG. 10B shows cellular activity data for the compound of Example 1 (i.e. CC-006) compared to known compounds in an HL60 cell line.
Figure 10A:
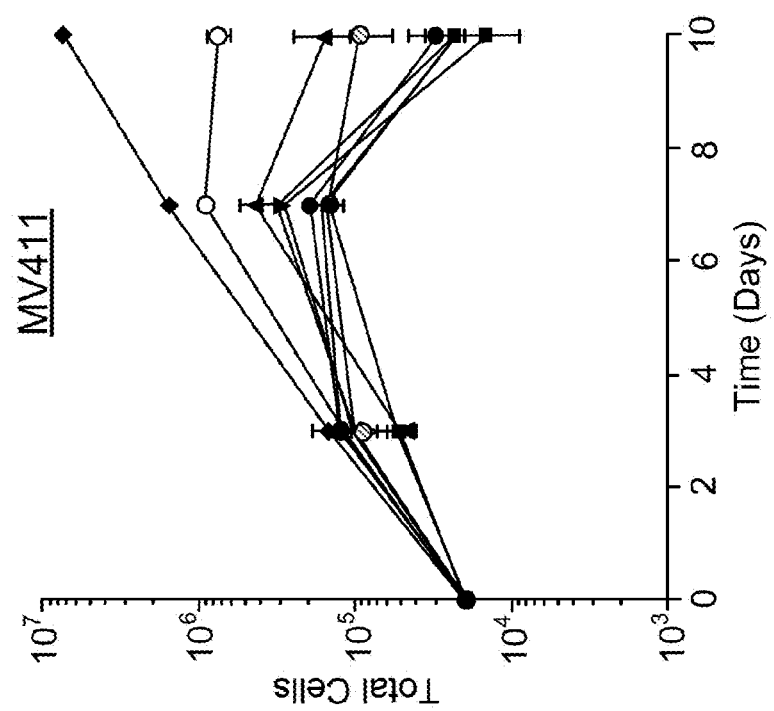
FIG. 10A shows cellular activity data for the compound of Example 1 (i.e. CC-006) compared to known compounds in a DOT1L related leukemia cell line (MV411).

An ALPHA assay developed based on probes described herein has shown excellent Z' (0.66), and is suitable for high through-put screening, as shown in FIG. 3. The assay has been used to test the DOT1L inhibitors provided herein and the results are in good agreement with DSF assay data. Biochemical assay data from an ALPHA screen (FIG. 9) further shows that the compound of Example 1 (i.e., CC-006) binds to DOT1L. The observed potency was similar to EPZ4777 and slightly less than EZP5676. Cellular activity was shown to be more potent than EPZ4777 on DOT1L related leukemia, but not on HL60, as shown in FIGS. 10A-B.

Materials

AlphaScreen Beads (Perkin Elmer #6760619M), Nickel chelate acceptor beads, Streptavidin donor beads, AlphaScreen Plates (Perkin Elmer #6005359), Plate Covers (Costar #6570), Alpha Buffer (50 mM HEPES, 150 mM NaCl, 0.1% w/v BSA, 0.01% w/v Tween20, pH 7.5, Store at 4°, allow to equilibrate to RT before beginning assay).

General Procedures

Two stock solutions are made at 2× the final concentration in Alpha buffer. The components of these 2× solutions are dependent on the biochemistry of the protein being assayed. All solutions containing Alpha beads should be handled in low light conditions. In general for 384 well assay formats, 10 μL of solution A is added to the 384 well alpha plate and the plate is spun at 1000 rpm for 30 s. The plate is incubated at room temperature, then 100 nL of test compounds are pinned into the plate, followed by a second incubation at room temperature. Finally, 10 μL of solution B is added to the 384 well alpha plate, the plate is spun down and incubated at room temperature and read on a plate reader.

General Plate Reader Settings

Plates can be read with an Envision plate reader, which comes with a predefined AlphaScreen program that has the correct excitation and emission wavelengths, cutoff filters, delay time, etc.

Specific Protocols

Step 1.

All reagents were diluted in standard alpha buffer with the below modifications and allowed to equilibrate to room temperature prior to addition to plates. After addition of Alpha beads to master solutions all subsequent steps were performed in low light conditions.

0.5% w/v BSA
0.05% w/v Tween20
pH=8.0
1 mM DTT added fresh

Step 2.

A 2× solution of his6-DOT1L+biotinylated probe is made such the final concentration of the components in the final assay volume of 20 μL is:

His6-DOT1L: 80 nM final concentration.
Biotin-FED1 (JQ-PROB2B): 40 nM final concentration.

Step 3.

10 μL of this solution is added to the 384 well plate and the plate is spun for 30 s at 1000 rpm.

Step 4.

100 nL of experimental compounds in DMSO is pinned into the 384 well assay plate, and the plate is spun again for 30 s at 1000 rpm.

Step 5.

Plates are incubated at room temperature for 30 minutes.

Step 6.

A 2× solution of alpha beads is made such the concentration of the components in the final assay volume of 20 μL is:

Nickel chelate acceptor bead: 25 μg/mL final concentration
Streptavidin donor bead: 25 μg/mL final concentration Step 7.

10 μL of this solution is added to the 384 well plate and the plate is spun for 30 s at 1000 rpm.

Step 8.

Plates are incubated at room temperature for 20 minutes, then read on plate reader.

Example 8

Cellular Assays

High Content Imaging Assay (HCI)

Figure 4:
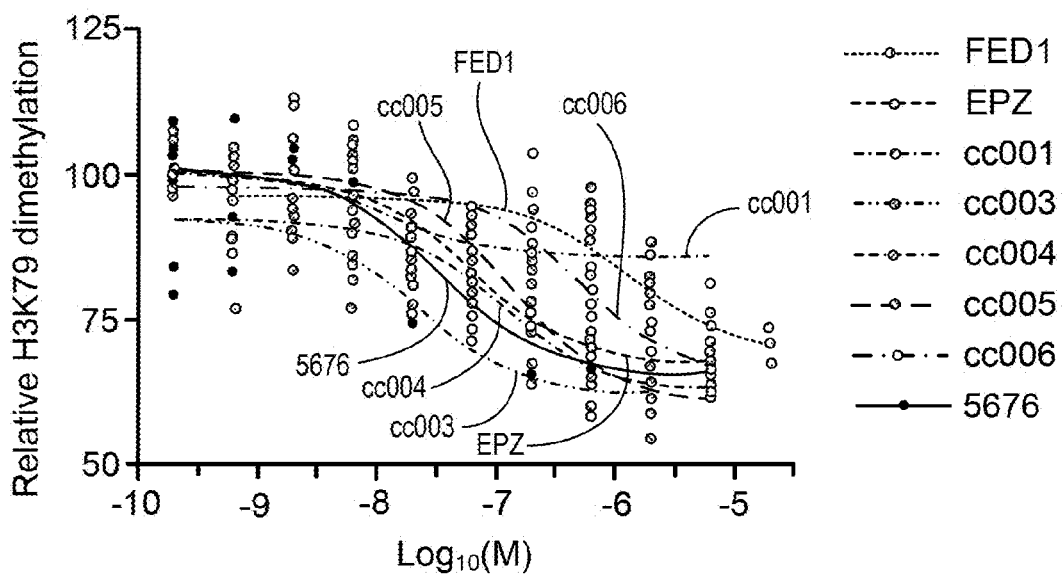
FIG. 4 shows the results of a High Content Imaging Assay (HCI).

The compounds of Examples 1-4 and known DOT1L inhibitors were analyzed in a High Content Imaging Assay (HCI). As shown in FIG. 4, the compounds provided herein (Examples 1-4) are more potent than previously disclosed compounds CC001 and CC002 (see U.S. 2014/0051654, structures shown below).

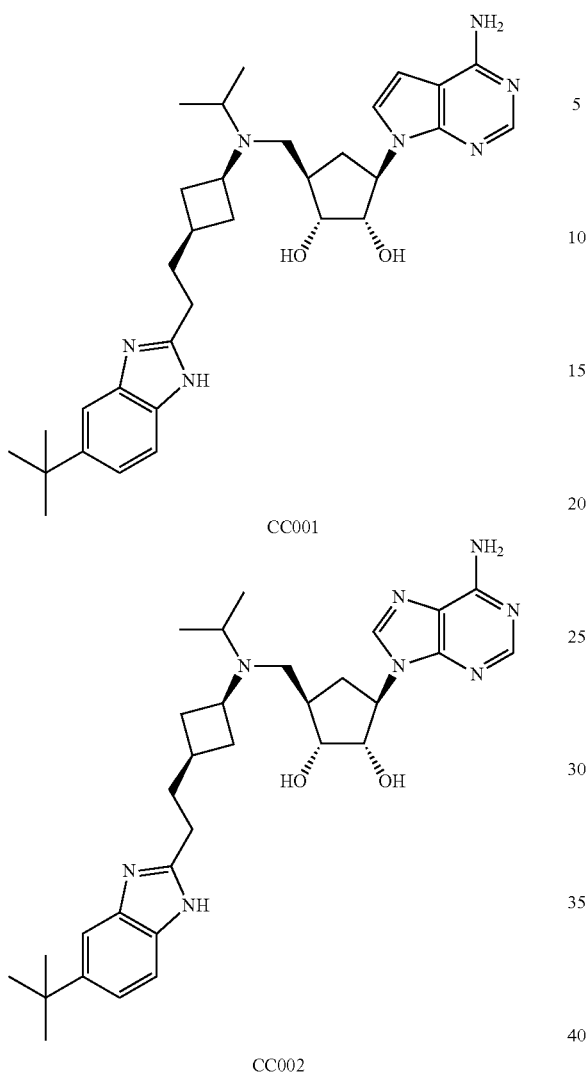

CC001

CC002

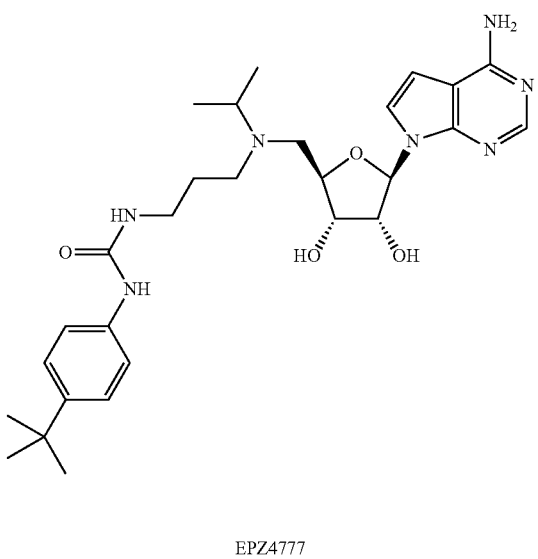

EPZ4777

Western Blot Assay

Figure 5:
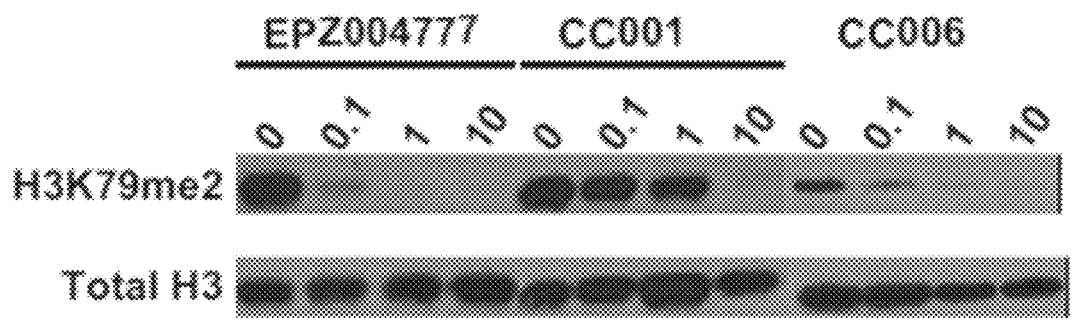
FIG. 5 shows the results of a Western blot Assay.

The western blot on the H3K27Me3 mark, as shown in FIG. 5 confirmed the compound of Example 1 (i.e. CC-006) can reduce the H3K27 trimethylation at much lower dose compared to known DOT1L inhibitors EPZ004777 (structure shown below) and CC001.

Gene Expression Assay

Figure 6:
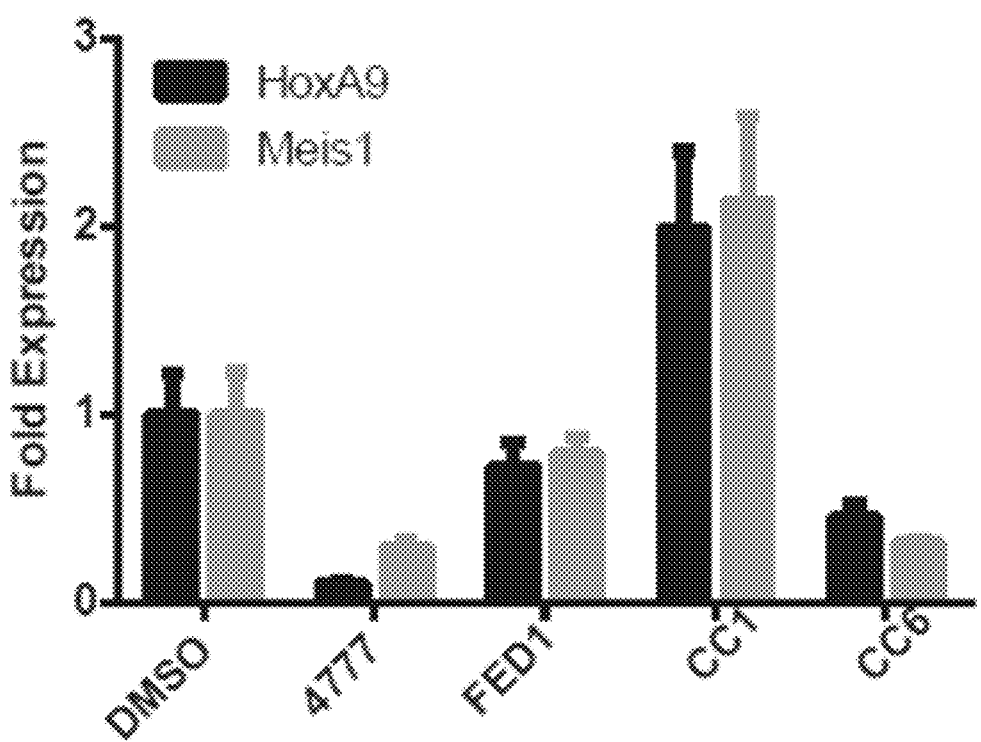
FIG. 6 shows the results of a Gene Expression Assay.

The results of the gene expression assay are shown in FIG. 6. The compound of Example 1 (i.e. CC-006) down regulates the related gene more efficiently than known DOT1L inhibitor CC001 and very similar to EPZ4777, which shows its on-target effect in cells.

Anti-Proliferation Study

Figure 7:
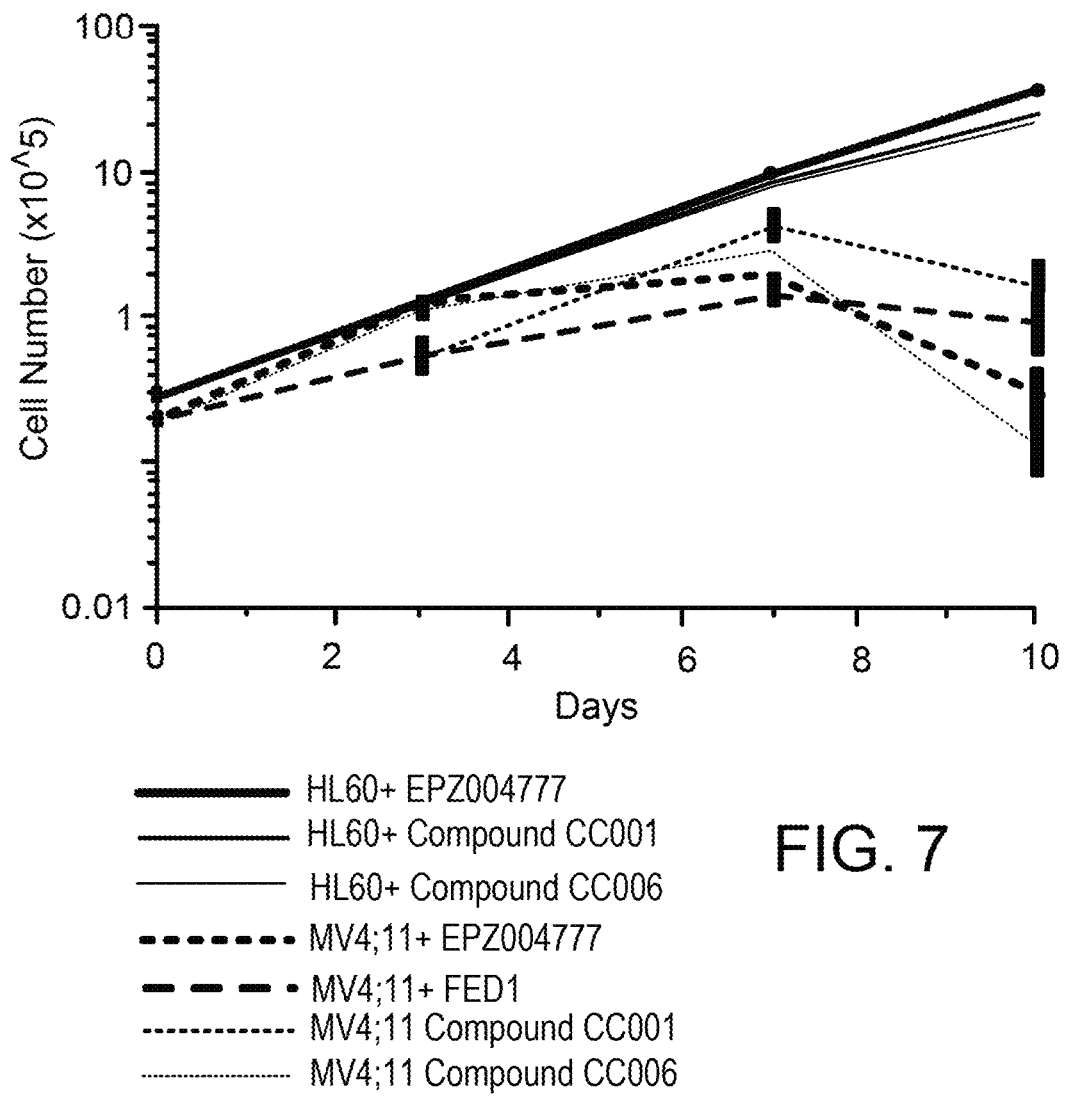
FIG. 7 shows the results of an anti-proliferation study of compounds in the MV4:11 cell line.

An anti-proliferation study of compounds in the MV4:11 cell line further confirmed that by installing CN group at the 7' position, the activity of the compound of Example 1 (i.e. CC-006) is greater than known DOT1L inhibitor CC001, as shown in FIG. 7. The compounds of Examples 2-4 also improved the activity but exhibited certain level of the toxicity against other cancer cell lines.

Example 9

Pharmacokinetic Studies

Pharmacokinetic studies of the compound of Example 1 (i.e. CC-006) and previously disclosed compounds EPZ004777, CC001 (see U.S. 2014/0051654) and FED1 were performed in CD1 mice following intravenous administration, as detailed in Table 1.

TABLE 1

| Category | Item | Description |
|---|---|---|
| Species | mouse | male CD1, N = 3 |
| Formulation | | see below[2] |
| In-Life | IP, 5 mg/kg, TBD mL/kg, N = 3 | Sampling at 0 min, 5, 15, 30 min, 1, 2, 4, 8 and 24 h, 9 time points for blood collection, serial bleeding, dosing via intraperitoneal, sampling via tail vein. |
| BioAnalytical | Method development | Bioanalytical method development in blood, parent only no metabolite. |
| | Sample analysis[1] | 27 blood samples, parent only, no metabolite. |

Figures 8A, 8B:
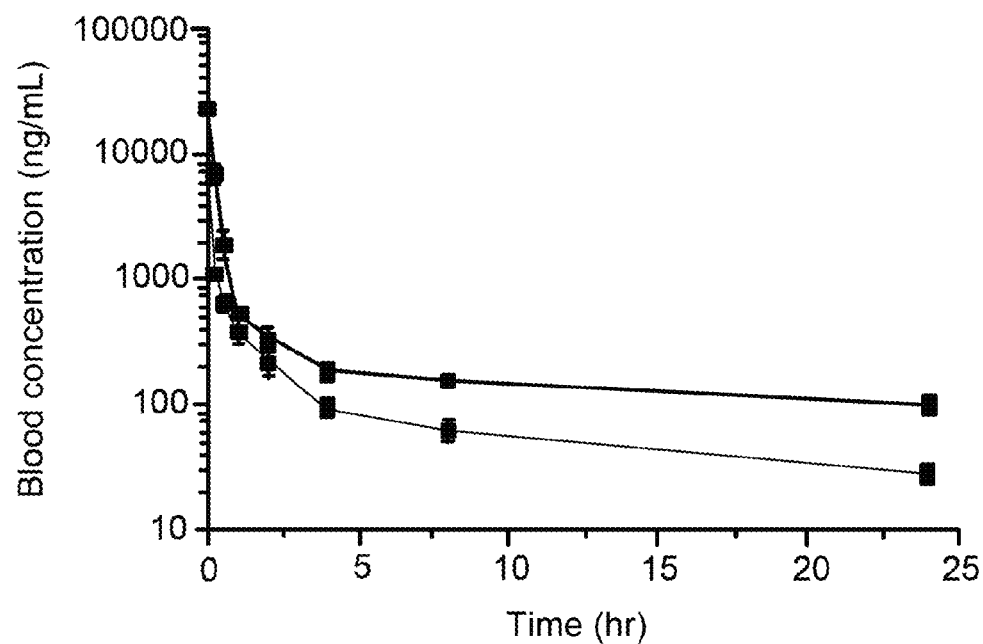
FIG. 8A shows mean plasma concentration-time profiles representative of the compound of Example 1 (i.e. CC-006) after intravenous dosing.
FIG. 8B shows the calculated pharmacokinetic parameters for intravenous administration of the compound of Example 1 (i.e. CC-006) and known DOT inhibitors.

[1] Target molecule concentration was determined by LC-MS and MS-MS.
[2] The formulation was prepared as an intravenous dosing solution at 1 mg/mL according to the following Mean plasma concentration-time profiles representative of the compound of Example 1 (i.e. CC-006) after intravenous dosing (5 mg kg$^{-1}$) are shown in FIG. 8A (data represent the mean and s.d. (n=3)). As shown in FIG. 8B, the calculated pharmacokinetic parameters for intravenous administration of the compound of Example 1 (i.e. CC-006) demonstrate good drug exposure (area under the curve (AUC)) and a half-life (T$_{1/2}$) of 12.6 h, approximately 4.3× the half-life of EPZ004777 and 10.5× the half-life of FED1. Though the half-life of CC001 exhibits the longest half-life of the compounds tested, the compound of Example 1 (i.e. CC-006) exhibits largely improved cellular activity compared to CC0001. From the pharmacokinetic properties, the compound of Example 1 (i.e. CC-006) has potential for use in treatment using intravenous administration due to its long half-life, as compared to subcutaneous administration.

Figure 11:
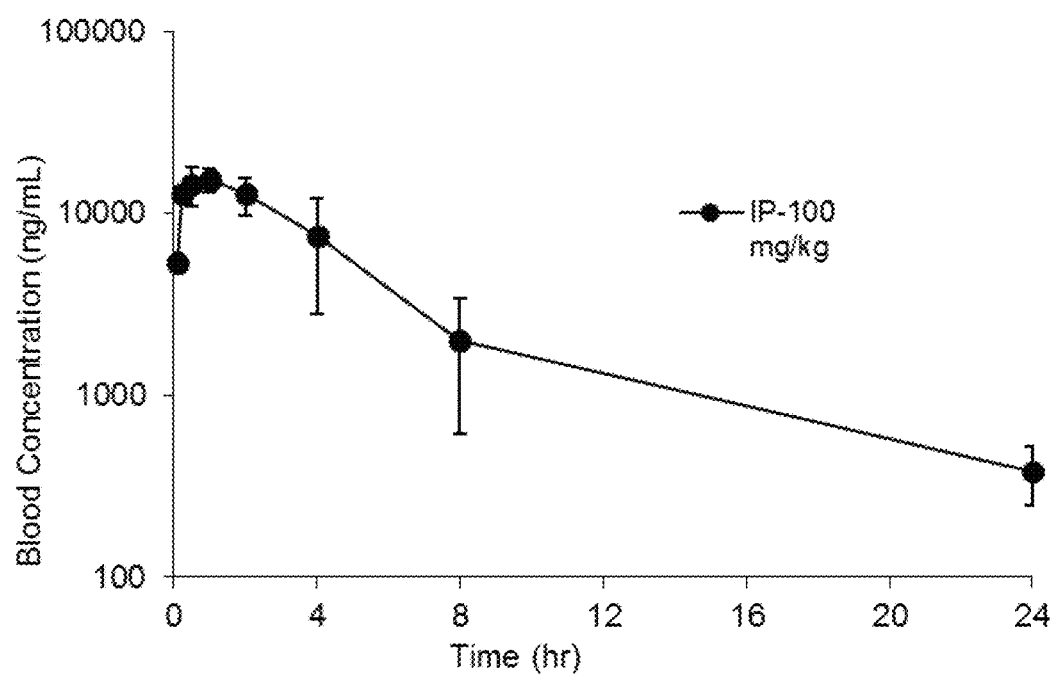
FIG. 11 shows the blood concentration of the compound of Example 1 (i.e. CC-006) in mice (IP dosage of 100 mg/kg) over 24 hours.

Pharmacokinetic studies in CD1 mice using the compound of Example 1 (i.e. CC-006) (100 mg/kg, IP dose) were also performed. Table 2 summarizes the individual and mean whole blood concentration-time data of the compound of Example 1 (i.e., CC-006) after an IP dose at 100 mg/kg in male CD1 mice and FIG. 11 shows mean whole blood concentration-time profiles of the compound of Example 1 after IP dose at 100 mg/kg (N=3/time point) in male CD1 mice.

TABLE 2

| Dose (mg/kg) | Dose route | Sampling time (hr) | Concentration (ng/mL) | | | Mean (ng/mL) | SD | CV (%) |
| --- | --- | --- | --- | --- | --- | --- | --- | --- |
| | | | Mouse#1 | Mouse#2 | Mouse#3 | | | |
| 100 | IP | 0 | BQL | BQL | BQL | BQL | NA | NA |
| | | 0.083 | 4597 | 5943 | 5504 | 5348 | 686 | 12.8 |
| | | 0.25 | 12006 | 13376 | 12784 | 12722 | 687 | 5.40 |
| | | 0.5 | 11074 | 14132 | 17841 | 14349 | 3389 | 23.6 |
| | | 1 | 13080 | 15012 | 17504 | 15199 | 2218 | 14.6 |
| | | 2 | 10506 | 11260 | 16086 | 12617 | 3028 | 24.0 |
| | | 4 | 4214 | 5377 | 12752 | 7448 | 4630 | 62.2 |
| | | 8 | 957 | 1458 | 3571 | 1995 | 1388 | 69.5 |
| | | 24 | 266 | 350 | 531 | 382 | 136 | 35.5 |
| PK parameters | Unit | | Mouse#1 | Mouse#2 | Mouse#3 | Mean | SD | CV (%) |
| T$_{max}$ | hr | | 1.00 | 1.00 | 0.500 | 0.833 | 0.289 | 34.6 |
| C$_{max}$ | ng/ml | | 13080 | 15012 | 17841 | 15311 | 2395 | 15.6 |
| Terminal t$_{1/2}$ | hr | | 4.64 | 4.80 | 4.51 | 4.65 | 0.142 | 3.04 |
| AUC$_{last}$ | hr * ng/ml | | 57137 | 70485 | 125522 | 84381 | 36248 | 43.0 |
| AUC$_{INF}$ | hr * ng/ml | | 58914 | 72904 | 128982 | 86933 | 37081 | 42.7 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I):

(I)

or a pharmaceutically acceptable salt thereof, wherein R$^1$ is selected from the group consisting of CN, halo, and C$_{1-4}$ haloalkyl.

2. The compound of claim 1, wherein R$^1$ is halo.

3. The compound of claim 1, wherein R$^1$ is chloro or bromo.

4. The compound of claim 1, wherein R$^1$ is chloro.

5. The compound of claim 1, wherein R$^1$ is bromo.

6. The compound of claim 1, wherein R$^1$ is C$_{1-4}$ haloalkyl.

7. The compound of claim 1, wherein R$^1$ is trifluoromethyl.

8. The compound of claim 1, wherein R$^1$ is CN.

9. The compound of claim 1, wherein the compound of Formula (I) is a compound of Formula (Ia):

(Ia)

or a pharmaceutically acceptable salt thereof.

10. The compound of claim 1, wherein the compound is selected from the group consisting of:

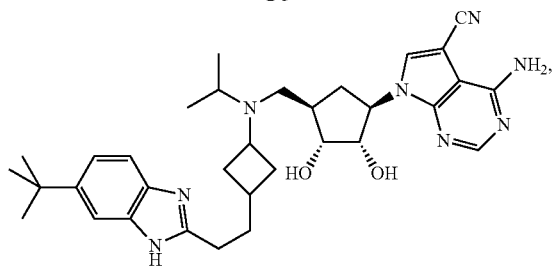

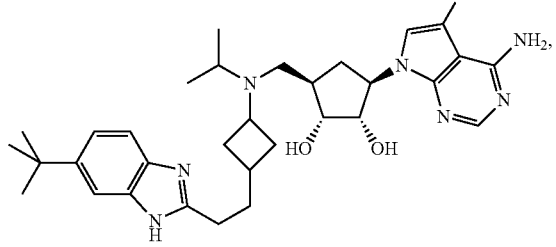

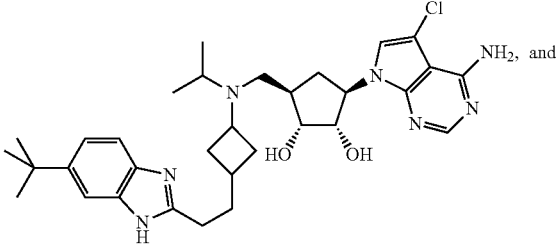

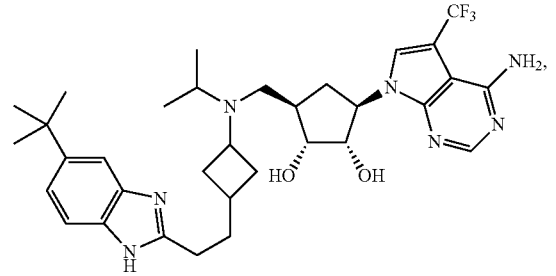 [SMILES: CC(C)N(C[C@H]1C[C@@H](n2cc(C(F)(F)F)c3c(N)ncnc32)[C@H](O)[C@@H]1O)C1CC(CCc2nc3cc(C(C)(C)C)ccc3[nH]2)C1]

or a pharmaceutically acceptable salt thereof.

11. The compound of claim 1, wherein the compound is:

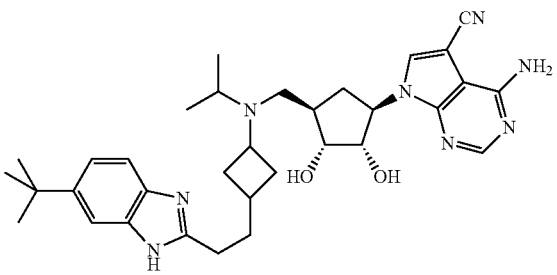

or a pharmaceutically acceptable salt thereof.

12. The compound of claim 1, wherein the compound has a biological half-life of from about 10 h to about 13 h.

13. A pharmaceutical composition comprising a compound of claim 1, or a pharmaceutically acceptable salt thereof, and at least one pharmaceutically acceptable carrier.

14. A method of inhibiting an activity of DOT1L, comprising contacting DOT1L with a compound of claim 1, or a pharmaceutically acceptable salt thereof.

15. A method of treating a disease in a patient, wherein said disease is selected from the group consisting of acute myeloid leukemia, acute lymphocytic leukemia, and mixed lineage leukemia, comprising administering to said patient a therapeutically effective amount of a compound of claim 1, or a pharmaceutically acceptable salt thereof.

* * * * *